(12) United States Patent
Briggs et al.

(10) Patent No.: US 7,186,230 B2
(45) Date of Patent: Mar. 6, 2007

(54) METHOD AND APPARATUS FOR THE CONTINUOUS SEPARATION OF BIOLOGICAL FLUIDS INTO COMPONENTS

(75) Inventors: Dennis A. Briggs, West Chester, PA (US); Michael Hutchinson, King of Prussia, PA (US)

(73) Assignee: Therakos, Inc, Exton, PA (US)

( * ) Notice: Subject to any disclaimer, the term of this patent is extended or adjusted under 35 U.S.C. 154(b) by 552 days.

(21) Appl. No.: 10/375,629

(22) Filed: Feb. 27, 2003

(65) Prior Publication Data

US 2003/0181305 A1  Sep. 25, 2003

Related U.S. Application Data

(60) Provisional application No. 60/361,287, filed on Mar. 4, 2002.

(51) Int. Cl.
 A61M 37/00 (2006.01)
 B04B 1/00 (2006.01)
 B04B 9/12 (2006.01)
 B01D 33/15 (2006.01)
 C02F 1/38 (2006.01)

(52) U.S. Cl. .................. 604/6.01; 604/6.16; 604/4.01; 494/43; 494/63; 210/782; 210/360.1; 210/363

(58) Field of Classification Search ............... 604/4.01, 604/6.01–6.08, 6.15, 6.16; 422/44–48; 494/1–9, 31–37, 43, 44, 60, 63, 85; 210/600, 210/767, 780–782, 294, 295, 319, 348, 359, 210/360.1, 369, 360.2, 398, 399, 361–363
See application file for complete search history.

(56) References Cited

U.S. PATENT DOCUMENTS

| | | |
|---|---|---|
| 3,145,713 A | 8/1964 | Latham, Jr. |
| 3,986,442 A | 10/1976 | Khoja et al. |
| 4,059,108 A | 11/1977 | Latham, Jr. |
| 4,086,924 A | 5/1978 | Latham, Jr. |
| 4,108,353 A | 8/1978 | Brown |
| 4,109,852 A | 8/1978 | Brown et al. |
| 4,109,854 A | 8/1978 | Brown |

(Continued)

FOREIGN PATENT DOCUMENTS

DE  38 17 664 A1  11/1989

(Continued)

*Primary Examiner*—Patricia Bianco
(74) *Attorney, Agent, or Firm*—Todd Volyn

(57) ABSTRACT

The present invention relates to systems, methods and apparatus for improving the yield for separating components of fluids, for example biological or sensitive fluids such as blood, and improving the component yield, for example, from donated whole blood by separating its components by density in a centrifuge bowl with a multi-axial lumen. The apparatus, system, and method eliminate the need to batch-type separate blood and can reduce the time needed to treat patients suffering from T-cell or white blood cell mediated diseases or conditions to less than 70 minutes. In one aspect, the invention is a centrifuge bowl (10) comprising an outer housing (100); a core (200); a lower plate (300); a lumen (400); a first bowl channel (420) within said lumen (400) for inflowing said fluid (800); a second bowl channel (410) for removing a first separated fluid component (810); and a third bowl channel (740) for removing a second separated fluid component (820).

6 Claims, 19 Drawing Sheets

U.S. PATENT DOCUMENTS

| | | | |
|---|---|---|---|
| 4,109,855 A | 8/1978 | Brown et al. |
| 4,111,356 A | 9/1978 | Boggs et al. |
| 4,114,802 A | 9/1978 | Brown |
| 4,120,449 A | 10/1978 | Brown et al. |
| 4,201,525 A | 5/1980 | Brown et al. |
| 4,204,537 A | 5/1980 | Latham, Jr. |
| 4,285,464 A | 8/1981 | Latham, Jr. |
| 4,300,717 A | 11/1981 | Latham, Jr. |
| 4,303,193 A | 12/1981 | Latham, Jr. |
| 4,305,659 A | 12/1981 | Bilstad et al. |
| 4,309,993 A | 1/1982 | Brown |
| 4,321,919 A | 3/1982 | Edelson |
| 4,333,016 A | 6/1982 | Bilstad et al. |
| 4,374,731 A | 2/1983 | Brown et al. |
| 4,389,206 A | 6/1983 | Bacehowski et al. |
| 4,398,906 A | 8/1983 | Edelson |
| 4,417,884 A | 11/1983 | Schoendorfer et al. |
| 4,421,503 A | 12/1983 | Latham, Jr. et al. |
| 4,425,116 A | 1/1984 | Bilstad et al. |
| 4,428,744 A * | 1/1984 | Edelson .................... 604/6.08 |
| 4,464,166 A | 8/1984 | Edelson |
| 4,479,760 A | 10/1984 | Bilstad et al. |
| 4,479,761 A | 10/1984 | Bilstad et al. |
| 4,479,762 A | 10/1984 | Bilstad et al. |
| 4,530,691 A | 7/1985 | Brown |
| 4,605,503 A | 8/1986 | Bilstad et al. |
| 4,680,025 A | 7/1987 | Kruger et al. |
| 4,724,317 A | 2/1988 | Brown et al. |
| 4,806,252 A | 2/1989 | Brown et al. |
| 4,834,890 A | 5/1989 | Brown et al. |
| 4,940,543 A | 7/1990 | Brown et al. |
| 5,076,911 A | 12/1991 | Brown et al. |
| 5,104,526 A | 4/1992 | Brown et al. |
| 5,240,614 A | 8/1993 | Ofsthun et al. |
| 5,316,666 A | 5/1994 | Brown et al. |
| 5,316,667 A | 5/1994 | Brown et al. |
| 5,322,620 A | 6/1994 | Brown et al. |
| 5,360,542 A | 11/1994 | Williamson, IV et al. |
| 5,370,802 A | 12/1994 | Brown |
| 5,427,509 A | 6/1995 | Chapman et al. |
| 5,427,695 A | 6/1995 | Brown |
| 5,462,416 A | 10/1995 | Dennehey et al. |
| 5,494,578 A | 2/1996 | Brown et al. |
| 5,494,592 A | 2/1996 | Latham, Jr. et al. |
| 5,514,069 A | 5/1996 | Brown et al. |
| 5,525,218 A | 6/1996 | Williamson, IV et al. |
| 5,527,467 A | 6/1996 | Ofsthun et al. |
| 5,529,691 A | 6/1996 | Brown |
| 5,538,405 A | 7/1996 | Patno et al. |
| 5,549,834 A | 8/1996 | Brown |
| 5,551,942 A | 9/1996 | Brown et al. |
| 5,573,678 A | 11/1996 | Brown et al. |
| 5,607,579 A | 3/1997 | Latham, Jr. et al. |
| 5,628,915 A | 5/1997 | Brown et al. |
| 5,632,893 A | 5/1997 | Brown et al. |
| 5,639,382 A | 6/1997 | Brown |
| 5,641,414 A | 6/1997 | Brown |
| 5,656,163 A | 8/1997 | Brown |
| 5,676,841 A | 10/1997 | Brown |
| 5,681,273 A | 10/1997 | Brown |
| 5,690,602 A | 11/1997 | Brown et al. |
| 5,690,835 A | 11/1997 | Brown |
| 5,693,232 A | 12/1997 | Brown et al. |
| 5,730,883 A | 3/1998 | Brown |
| 5,750,039 A | 5/1998 | Brown et al. |
| 5,759,413 A | 6/1998 | Brown |
| 5,792,372 A | 8/1998 | Brown et al. |
| 5,804,079 A | 9/1998 | Brown |
| 5,807,492 A | 9/1998 | Brown et al. |
| 5,833,866 A | 11/1998 | Brown |
| 5,849,203 A | 12/1998 | Brown et al. |
| 5,945,291 A | 8/1999 | Bolton et al. |
| 5,958,250 A | 9/1999 | Brown et al. |
| 5,961,842 A | 10/1999 | Min et al. |
| 5,980,757 A | 11/1999 | Brown et al. |
| 5,980,760 A | 11/1999 | Min et al. |
| 5,993,370 A | 11/1999 | Brown et al. |
| 5,996,634 A | 12/1999 | Dennehey et al. |
| 6,007,725 A | 12/1999 | Brown |
| 6,027,657 A | 2/2000 | Min et al. |
| 6,059,979 A | 5/2000 | Brown |
| 6,071,421 A | 6/2000 | Brown |
| 6,071,423 A | 6/2000 | Brown et al. |
| 6,183,651 B1 | 2/2001 | Brown et al. |
| 6,197,202 B1 | 3/2001 | Brown |
| 6,204,058 B1 | 3/2001 | Bolton |
| 6,207,063 B1 | 3/2001 | Brown |
| 6,228,017 B1 | 5/2001 | Brown |
| 6,261,065 B1 | 7/2001 | Nayak et al. |
| 6,296,450 B1 | 10/2001 | Westberg et al. |
| 6,312,607 B1 | 11/2001 | Brown et al. |
| 6,322,488 B1 | 11/2001 | Westberg et al. |
| 6,495,366 B1 | 12/2002 | Briggs |
| 6,709,377 B1 | 3/2004 | Rochat |

FOREIGN PATENT DOCUMENTS

| | | | |
|---|---|---|---|
| EP | 0 297 216 B1 | | 1/1989 |
| EP | 0297216 B1 | * | 3/1992 |
| EP | 0786324 | | 7/1997 |
| EP | 1 066 842 A2 | | 1/2001 |
| WO | WO97/36581 | * | 10/1997 |
| WO | WO 97/36581 | | 10/1997 |
| WO | WO 97/36634 | | 10/1997 |

* cited by examiner

METHOD AND APPARATUS FOR THE CONTINUOUS SEPARATION OF BIOLOGICAL FLUIDS INTO COMPONENTS

CROSS-REFERENCE TO RELATED APPLICATION

This application claims the benefit of U.S. Provisional Application Ser. No. 60/361,287, filed Mar. 4, 2002.

TECHNICAL FIELD OF THE INVENTION

The present invention generally relates to methods and apparatus for separating a fluid into its components, for example, a biological or sensitive fluid such as blood, and specifically to methods and apparatus that use centrifugal force to separate a fluid into its components by density so as to improve the component yield.

BACKGROUND ART

With the advance of medical sciences, it has become possible to treat a patient's blood in closed-loop processes, returning the patient's own treated blood back to him in one medical treatment. An example of such processes include external treatment methods for diseases in which there is a pathological increase of lymphocytes, such as cutaneous T-cell lymphoma or other diseases affecting white blood cells. In such methods, the patient's blood is irradiated with ultraviolet light in the presence of a chemical or an antibody. Ultraviolet light affects the bonding between the lymphocytes and the chemical or antibody that inhibits the metabolic processes of the lymphocytes.

During one of these medical treatments, a centrifuge bowl, such as, for example, a Latham bowl, as shown in U.S. Pat. No. 4,303,193, expressly incorporated by reference in its entirety herein, separates blood into red blood cells ("RBCs") and buffy coat. The Latham bowl is a blood component separator that has been used for some time in the medical apheresis market as well as in innovative medical therapies such as extracorporeal photopheresis (ECP). PCT Applications WO 97/36581 and WO 97/36634, and U.S. Pat. Nos. 4,321,919; 4,398,906; 4,428,744; and 4,464,166 provide descriptions of extracorporeal photopheresis, and are hereby expressly incorporated by reference in their entirety.

The Latham bowl efficiency is often measured by the white blood cell ("WBC") "yield," which is typically about 50%. Yield is defined as the percentage of cells collected versus the number processed. When compared to other types of whole blood separators, this high yield enables the Latham bowl separator to collect much larger volumes of WBCs while processing much less whole blood from the donor patient. However, a major drawback to the Latham bowl separator is that the separation process must be repeatedly stopped to remove the packed RBCs and plasma once they fill the inside of the bowl, creating a "batch-type" process. Although the Latham bowl separator has a high volume yield, the constant filling and emptying of this bowl wastes time; thus, the process is considered less efficient with respect to time. Additionally, the Latham bowl requires a rotating seal, which is expensive and difficult to manufacture.

An additional drawback of centrifugal processing apparatus has been their high cost of manufacture due to strict tolerances, rotating seals, and extensive manufacturing processes.

DISCLOSURE OF INVENTION

An object of the present invention is to provide methods and apparatus for separating a fluid, such as blood or other biological fluid, into its components. An additional object is to increase the efficiency of current fluid separation processes by decreasing the time necessary to separate out a desired amount of a fluid component from the fluid. Yet other objects of the present invention are to treat a patient more efficiently, to improve a photopheresis process, to improve a platelet removal process, or to create a more efficient manufacture of a centrifuge bowl. Still another object of the present invention may include improved or more elegant rotation of a centrifuge bowl. An additional object of the present invention is to separate and remove targeted cells by their specific gravity. Another object of the present invention is to eliminate the need to perform fluid separation processes in "batch" form. A still further object of the present invention is to increase the percent yield of a desired fluid component from a fluid being separated.

Additionally, the present invention solves the inadequacies of the prior art by being able to continuously separate fluid components without interrupting the process to empty a centrifuge bowl and remove a separated component. Thus, the present invention eliminates batch processing and other Latham bowl batch-type techniques.

In a particular embodiment of the present invention, a centrifuge bowl may be used in conjunction with a photopheresis process. In extracorporeal photopheresis, for example, there are three phases including 1) the collection of a buffy coat fraction (leukocyte-enriched), 2) irradiation of the collected buffy coat fraction, and 3) reinfusion of the treated white blood cells. Extracorporeal photopheresis may be utilized to treat numerous diseases including Graft-versus-Host disease, Rheumatoid Arthritis, Progressive Systematic Sclerosis, Juvenile Onset Diabetes, Inflammatory Bowel Disease and other diseases that are thought to be T-cell or white blood cell mediated, including cancer.

The apparatus, methods, and systems of the present invention may be used in conjunction with methods for ameliorating or preventing Graft-versus-Host disease in a subject undergoing ectoderm cell transplant, endoderm cell transplant, and/or mesenchymal cell transplant, comprising the step of treating the subject with extracorporeal photopheresis prior to undergoing the ectoderm cell transplant, endoderm cell transplant, and/or mesenchymal cell transplant.

Further, the apparatus, methods, and systems of the present invention may be used in conjunction with methods and systems for ameliorating or preventing organ transplant rejection in a subject undergoing an organ transplant comprising the step of treating the subject with extracorporeal photopheresis prior to undergoing the organ transplant. The organ transplant may be a syngeneic graft, an allograft, or a xenograft. The organ may be a liver, a kidney, a heart, a lung, a pancreas, pancreatic islets, or the skin. The organ may be human, artificial, clonal, or mammalian.

The apparatus, methods, and systems of the present invention may also be used in conjunction with methods for ameliorating or preventing tissue transplant rejection in a subject undergoing a tissue transplant. The tissue graft may be an autograft, a syngeneic graft, an allograft, or a xenograft. The tissue may be cartilage, bone, liver, small-bowel, neuronal, adrenal medullary tissue, fetal thymus tissue, or parathyroid tissue. The tissue may be human, artificial, clonal, or mammalian.

Additionally, the apparatus, methods, and systems of the present invention may be used in conjunction with methods for preventing the onset, delaying the onset, ameliorating the effects, or ameliorating the potential severity of an autoimmune disease in a subject predisposed to an autoimmune disease, such as: Alopecia Areata, Ankylosing Spondylitis, Antiphospholipid Syndrome, Autoimmune Addison's Disease, Autoimmune Hemolytic Anemia, Autoimmune Hepatitis, Behcet's Disease, Bullous Pemphigoid, Cardiomyopathy, Celiac Sprue-Dermatitis, Chronic Fatigue Immune Dysfunction Syndrome (CFIDS), Chronic Inflammatory Demyelinating Polyneuropathy, Churg-Strauss Syndrome, Cicatricial Pemphigoid, CREST Syndrome, Cold Agglutinin Disease, Crohn's Disease, Discoid Lupus, Essential Mixed Cryoglobulinemia, Fibromyalgia-Fibromyositis, Graves' Disease, Guillain-Barré Syndrome, Hashimoto's Thyroiditis, Idiopathic Pulmonary Fibrosis, Idiopathic Thrombocytopenia Purpura (ITP), IgA Nephropathy, Insulin Dependent Diabetes, Juvenile Arthritis, Lichen Planus, Ménière's Disease, Mixed Connective Tissue Disease, Multiple Sclerosis, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis, Sarcoidosis, Scleroderma, Sjögren's Syndrome, Stiff-Man Syndrome, Systematic Lupus Erythematosus, Takayasu Arteritis, Temporal Arteritis/Giant Cell Arteritis, Ulcerative Colitis, Uveitis, Vasculitis, Vitiligo, and Wegener's Granulomatosis.

The present invention may also be used to separate and collect platelets from a donor, or to separate and remove other types of specific cells from a donor, such as, for example, diseased or abnormal cells.

Moreover, the apparatus, methods, and systems of the present invention may be used in conjunction with methods and systems for inducing apoptosis of cells. Apoptosis is a programmed cell death which results in the apoptic cells disintegrating and being phagocytosed while not becoming disrupted. Apoptosis has been proposed as a mechanism to treat autoimmune diseases by re-infusing the apoptic cells back into the host body, as described in U.S. Pat. Nos. 5,945,291 and 6,204,058, both of which are incorporated herein by reference.

Additional objects and advantages of the invention will be set forth in part in the description that follows, and in part will be obvious from the description, or may be learned by practice of the invention. The objects and advantages of the invention will be realized and attained by means of the elements and combinations particularly pointed out in the appended claims.

In one aspect, the invention is an apparatus for separating components of a fluid, the apparatus comprising: an outer housing with an upper housing end and a lower housing end, wherein said outer housing increases in diameter from said upper housing end to said lower housing end, said lower housing end having a housing floor and said housing upper end having a housing outlet, said outer housing having an interior volume and adapted for rotation about a center axis; a core connected with said outer housing for rotation therewith; said core having an outer wall having an upper core end and a lower core end, said lower core end having a core floor and said upper core end having a core outlet; said core occupying a coaxial volume of said interior volume of said outer housing and forming a separation volume between said core and said outer housing; a lower plate having a top surface, said lower plate positioned within said separation volume, beneath said core floor and above said housing floor; a lumen positioned inside said core, said lumen extending axially through said core; a first bowl channel within said lumen to said top surface of said lower plate for inflowing said fluid; a second bowl channel from within said separation volume beneath said lower plate for removing a first separated fluid component; and a third bowl channel from said separation volume above said lower plate for removing a second separated fluid component.

It is preferable that said outer wall of said core increases in diameter from said upper core end to said lower core end. Additionally, said second bowl channel and said third bowl channel can be positioned within said lumen so as to form a multi-axial lumen.

The apparatus of the present invention can further comprise a connection sleeve that is adapted to be secured to said apparatus near said housing outlet for rotation therewith. The connection sleeve is adapted to fluidly connect each of the first, second, and third bowl channels to a corresponding conduit channel of an external conduit. The connection sleeve can be adapted to be secured to said lumen or to said core. Preferably, the connection sleeve will also comprise a sleeve flange, and said housing outlet will be adapted to retain said sleeve flange.

It is further preferable that said lumen have an upper lumen end and a lower lumen end, and that said lumen increase in diameter from said upper lumen end to said lower lumen end. The core will preferably comprises a neck fitted around said lumen. Additionally, the core floor can comprise a floor flange that extends into said separation volume. This floor flange is adapted to guide the flow of said second separated fluid component upward into said separation volume while allowing said first separated fluid component to flow to said housing floor.

It is also preferable that the lower plate be circular and that said lumen and said floor of said core be a single structure. The apparatus is also designed so as to be closed to undesired contagions. Alternatively, the apparatus can be adapted to allow rotation of said core, said lower plate, and said outer housing about said lumen.

In order to be used to separate said fluid into said first and second components, the apparatus will further comprise a means for rotating said outer housing about said axis. Said outer housing will preferably comprise a locking mechanism adapted to secure said outer housing to said means for rotating. The locking mechanism can comprise protrusions and/or key slots that engage the outer housing to the means for rotating. It is further preferred that said means for rotating comprises a bracket that is adapted to engage and rotate an external conduit that is fluidly connected to said first bowl channel, said second bowl channel, and said third bowl channel. As such, the rotation means can be adapted to rotate said outer housing and said external conduit using 1-omega/2-omega spin technology, as is discussed in U.S. Pat. No. 3,986,442, which is incorporated by reference in its entirety herein. Thus, a rotatable seal is not required.

The elimination of the rotating fluid seal from the centrifuge bowl reduces cost and cell damage, enables longer cell processing times, and increases the survival and storage time for platelets and packed RBCs. Additionally, the elimination of the rotating seal and replacement with a completely sealed system reduces the likelihood of contamination or a hazardous biological spill. Further, the rotating seal has typically been a weak point in the machinery in terms of performance lifetime, complexity and fragility of its parts, and the necessity for a continuous and comparable degree of lubrication. During on-line blood separation, as applied to the collection of blood cells, rotating seals become critical in terms of platelet injury, red cell hemolysis, and obstruction of channels by aggregates and impaired lubrication of the rotating seals.

The apparatus can be economically fabricated from plastic by known molding techniques while maintaining tight tolerances. This results in the apparatus being manufactured inexpensively.

In yet another embodiment, the apparatus further comprises: means to remove said fluid from a source, said means to remove said fluid fluidly connected to said first bowl channel; means to remove said first separated fluid component via said second bowl channel; means to remove said second separated fluid component via said third bowl channel; and means to treat said second separated fluid component subsequent to being removed via said third bowl channel. In this embodiment, it is preferable that the apparatus also have a means to reinfuse treated second separated fluid component and said first separated fluid component back into said source, wherein said apparatus is a closed-loop apparatus when connected to said source.

Preferably, the source is a patient and the fluid is blood. In such a case, both the reinfusion means and the means to remove said fluid from said source will comprise a needle or a catheter. When the fluid is blood, the apparatus should further comprise an anticoagulant source fluidly connected between said means to remove said fluid from said source and said first bowl channel. Moreover, the means to remove said first separated fluid component via said second bowl channnle can be a pump that provides substantially stable flow, as disclosed, for example, in U.S. patent application Ser. No. 09/389,463, which is incorporated by reference in its entirety herein. It is preferred that said treatment means comprise a chamber and a source of ultraviolet radiation.

In another aspect, the invention is an improved connection sleeve for fluidly connecting an external conduit having a first conduit channel to a centrifuge bowl having a first bowl channel. The connection sleeve comprises: a body having an upper sleeve end and a lower sleeve end, said lower sleeve end adapted to be secured to said centrifuge bowl; a stub having a first stub channel extending therethrough, wherein said first stub channel is adapted to form a first passageway from said first conduit channel to said first bowl channel; a wall surrounding said stub near said upper sleeve end; and a trench between said wall and said stub, said trench adapted to receive and hold said external conduit. This improved connection sleeve is more durable than prior art connection sleeves and can better withstand cyclical rotational forces without failing.

The connection sleeve can comprise a sleeve flange positioned on said lower sleeve end, wherein said sleeve flange is adapted to engage said centrifuge bowl. Also preferably, the trench will be tapered and the body will increase in diameter from said upper sleeve end to said lower sleeve end. In this embodiment, it is further preferable that the wall be raised above said stub. In order to accommodate the inflow of said fluid and the outflow of said first and second separated fluid components, it is preferable that said stub further comprise second and third stub channels extending therethrough, said second and third stub channels adapted to form second and third passageways from second and third conduit channels to second and third bowl channels. The connection sleeve can be overmolded to said external conduit.

In yet another aspect, the invention is a method for separating components of a fluid into higher and lower density components, the method comprising: providing a centrifuge bowl comprising a first bowl channel, a second bowl channel, and a third bowl channel; flowing said fluid from a source into said centrifuge bowl through said first bowl channel; rotating said centrifuge bowl about an axis; removing said higher density component from said bowl via said second bowl channel; and removing said lower density component from said bowl via said third bowl channel concurrently with said removing of said higher density component.

In practicing this inventive method, it is preferable that the centrifuge bowl be constructed as described in detail above. Said higher density component can be removed via said second bowl channel by applying negative pressure to said second bowl channel with a pump. This pump should be adapted so as to provide substantially stable flow of said higher density component. Alternatively, said higher density component can be removed via said second bowl channel by applying positive pressure to said centrifuge bowl, forcing said higher density component out of the centrifuge bowl.

The inventive method can be performed using a biological fluid as the fluid, preferably blood. When blood is used, said higher density component comprises red blood cells and said lower density component can comprise a buffy coat. Thus, the inventive method can be used to collect platelets. The red blood cells can then be continuously reinfused into a source, such as a patient.

In another embodiment, the inventive method will comprise the further steps of: treating said lower density component; and reinfusing said treated lower density component into said source to treat, ameliorate, prevent, or delay the onset of diseases. The treatment can be continuous and the source can be a patient. Because the method can be performed continuously without the need to batch process said fluid, patient treatment time can be greatly reduced, and treatment can be completed in less than 70 minutes. The higher density component can be continuously reinfused into a source, such as a patient.

The method can be used to treat white blood cell and T-cell mediated diseases selected from the group consisting of cancer, T-cell lymphoma, Graft-versus-Host disease, Rheumatoid Arthritis, Progressive Systematic Sclerosis, Juvenile Onset Diabetes, Inflamatory Bowel Disease, Alopecia Areata, Ankylosing Spondylitis, Antiphospholipid Syndrome, Autoimmune Addison's Disease, Autoimmune Hemolytic Anemia, Autoimmune Hepatitis, Behcet's Disease, Bullous Pemphigoid, Cardiomyopathy, Celiac Sprue-Dermatitis, Chronic Fatigue Immune Dysfunction Syndrome, Chronic Inflammatory Demyelinating Polyneuropathy, Churg-Strauss Syndrome, Cicatricial Pemphigoid, CREST Syndrome, Cold Agglutinin Disease, Crohn's Disease, Discoid Lupus, Essential Mixed Cryoglobulinemia, Fibromyalgia-Fibromyositis, Graves' Disease, Guillain-Barré Syndrome, Hashimoto's Thyroiditis, Idiopathic Pulmonary Fibrosis, Idiopathic Thrombocytopenia Purpura, IgA Nephropathy, Insulin Dependent Diabetes, Juvenile Arthritis, Lichen Planus, Ménière's Disease, Mixed Connective Tissue Disease, Multiple Sclerosis, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis, Sarcoidosis, Scleroderma, Sjögren's Syndrome, Stiff-Man Syndrome, Systematic Lupus Erythematosus, Takayasu Arteritis, Temporal Arteritis/Giant Cell Arteritis, Ulcerative Colitis, Uveitis, Vasculitis, Vitiligo, and Wegener's Granulomatosis.

Additionally, the inventive method can be used to ameliorate or prevent organ or tissue transplant rejection. Preferably, said treatment step will comprise irradiating said lower density component. Moreover, the inventive method can be performed to induce apoptosis within said lower density component.

In yet another aspect, the present invention is a conduit assembly for fluidly connecting a source of fluid to a centrifuge bowl, the conduit assembly comprising: an external conduit of approximately constant diameter having a first conduit end and a second conduit end; a connection sleeve secured to said first conduit end, said connection sleeve adapted to fluidly connect to said centrifuge bowl; an anchor sleeve secured to said second conduit end; a first bearing ring surrounding said external conduit and positioned between said connection sleeve and said anchor sleeve, said first bearing ring adapted to engage a means for rotating said centrifuge bowl; and a first assembly channel extending through said conduit assembly. The conduit assembly of the present invention is inexpensive and easy to manufacture, allows easy optimization, and has improved durability.

Preferably, the connection sleeve and the anchor sleeve will be overmolded to said external conduit. The anchor sleeve can have a first anchor end and a second anchor end wherein the first anchor end is secured to said external conduit. The anchor sleeve can increase in diameter from said first anchor end to said second anchor end. It is further preferable that the connection sleeve have an upper sleeve end and a lower sleeve end, wherein said upper sleeve end of said connection sleeve is secured to said external conduit, and said connection sleeve increased in diameter from said upper sleeve end to said lower sleeve end.

In this embodiment, the connection sleeve will preferably have a wall surrounding a stub near said upper sleeve end. The connection sleeve will further have a trench between said wall and said stub, wherein said trench is adapted to receive and secure said external conduit. Preferably, the trench is tapered and the wall is raised above said stub. Also, the connection sleeve will further comprise a sleeve flange.

Because the conduit assembly can be used to inflow a fluid and outflow two separated fluid components, the conduit assembly will preferably also comprise a second assembly channel and a third assembly channel. In order to reduce wear of the conduit assembly, the conduit assembly can further comprise a second bearing ring surrounding said conduit and positioned between said first bearing ring and said anchor sleeve. This second bearing ring will be adapted to engage a means for rotating said centrifuge bowl. The first and second bearing rings should be 7.5 to 9.5 inches apart, wherein the first bearing ring is 5.0 to 5.5 inches from the lower end of said connection sleeve.

It is understood that both the foregoing general description and the following detailed description are exemplary and explanatory only and are not restrictive of the invention as claimed. The accompanying drawings illustrate several embodiments of the invention and together with the description serve to explain the principles of the invention.

MODES FOR CARRYING OUT THE INVENTION

Reference will now be made in detail to the present preferred or exemplary embodiments of the invention, examples of which are illustrated in the accompanying drawings.

In a specific embodiment, the present invention relates to methods and apparatus that separate fluid components, such as, for example, the components of a biological fluid by density or weight. Biological fluids encompass fluids that comprise, exist in, or are used in, or delivered to living organisms. Indeed, biological fluids may comprise bodily fluids and their components, such as blood cells, plasma, and other fluids that comprise biological components, including living organisms such as bacteria, cells, or other cellular components. Biological fluids may also comprise whole blood or specific whole blood components, including red blood cells, platelets, white blood cells, and precursor cells. In particular, it may be desirable to remove blood from a patient for treatment, such as for example, extracorporeal treatment. It is to be understood, however, that the present invention is adaptable to use with various centrifugal processing apparatus, and the specific example given herein is merely for illustrative purposes. Other uses for the separation techniques and apparatus may include other medical processes such as dialysis, chemotherapy, platelet separation and removal, and separation and removal of other specific cells. Additionally, the present invention may be used to separate other types of fluids that include a wide variety of non-medical uses, such as, for example, oil and fluid component separation. All components used in the present invention should not adversely affect biological fluids or render them unsuitable for their intended uses, such as those described herein and may be made of any suitable material compatible with uses described herein including, but not limited to plastics, such as polycarbonate, methyl methacrylate, styrene-acrylonitrile, acrylic, styrene, acrylonitrile or any other plastic.

Figure 1:
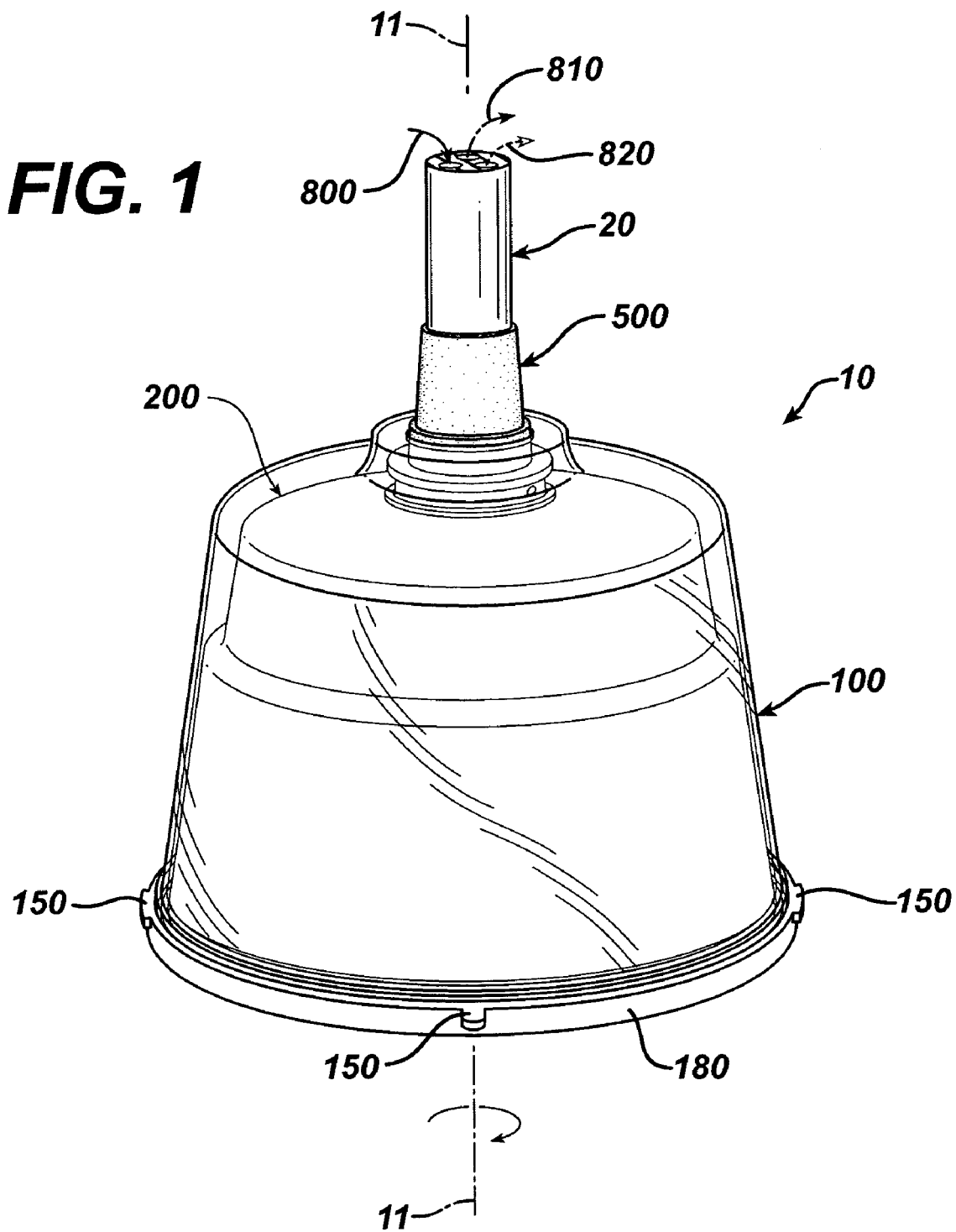
FIG. 1 is a front elevational view of an embodiment a centrifuge bowl, a connection sleeve, and a portion of an external conduit according to the present invention.

To achieve the objects in accordance with the purpose of the invention, as embodied and broadly described herein, FIG. 1 depicts a specific embodiment of the invention. The embodiment of the present invention depicted in FIG. 1 comprises a centrifuge bowl 10 in fluid connection with connection sleeve 500. Lower sleeve end 832 (FIG. 7) of connection sleeve 500 is secured to bowl 10. Upper sleeve end 831 of connection sleeve 500 is secured to external conduit 20, thus fluidly connecting external conduit 20 to bowl 10. This fluid connection enables fluid 800 to be supplied through external conduit 20 to bowl 10. Similarly, this fluid connection also enables separated fluid components 810, 820 to be removed from bowl 10 through external conduit 20. Bowl 10 is adapted to be rotated around its center axis 11.

Figure 12:
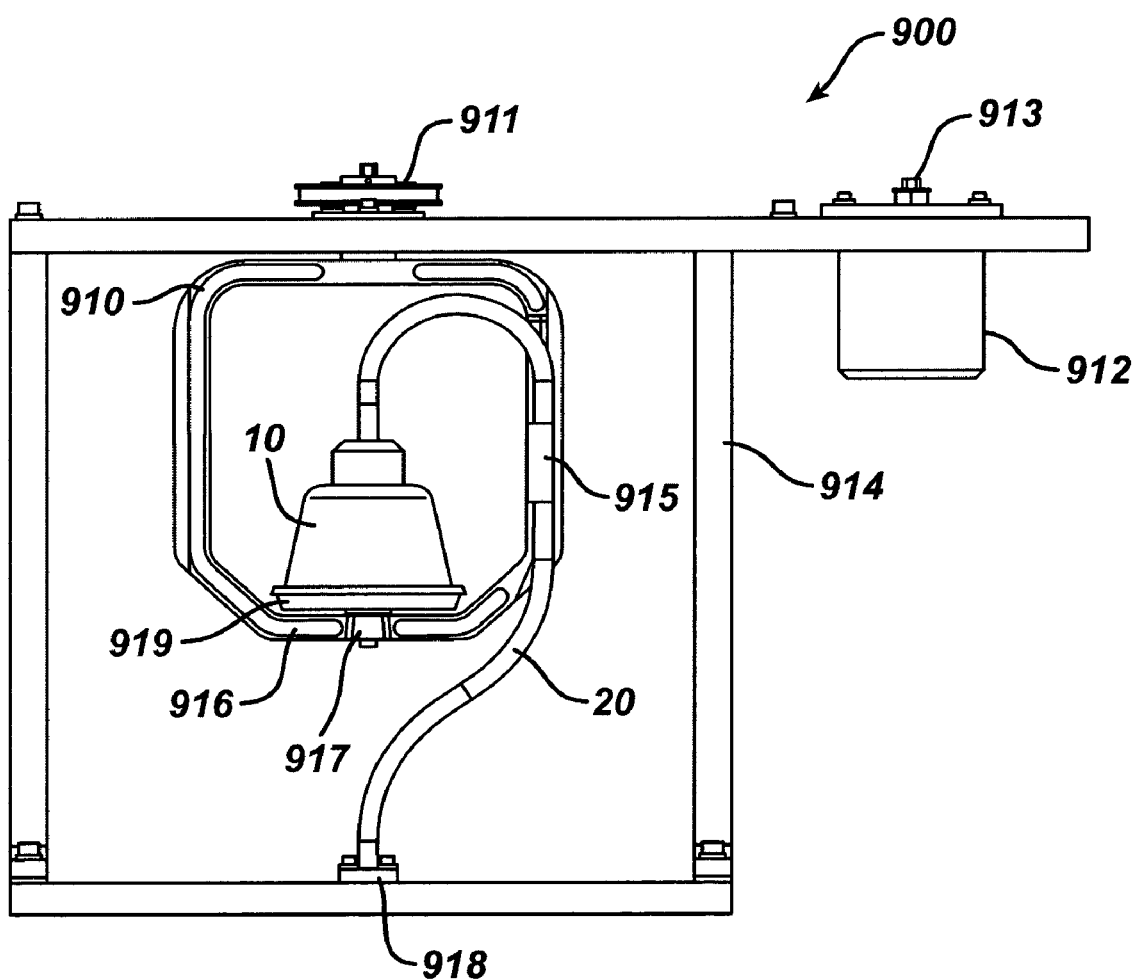
FIG. 12 is a schematic of an embodiment of the apparatus of FIG. 1 positioned in a 1-omega 2-omega rotational device.

Bowl 10 comprises outer housing 100 and core 200. As illustrated, outer housing 100 is constructed of clear plastic so that core 200 is visible therethrough. Outer housing 100 comprises housing floor 180 which in turn comprises protrusions 150 for locking bowl 10 into rotational device 900 (FIG. 12). Bowl 10 is preferably simplified in construction and is easy to manufacture by molding or other known manufacturing processes, such that it may be disposable or used for a limited number of treatments, and is most preferably capable of containing about 125 ml of fluid, such fluid possibly being pressurized. In alternative embodiments, the volume capacity of the bowl may vary depending upon the health of the patient and his or her allowable extracorporeal volume. The volume capacity of the bowl may also vary depending upon the use of the bowl or the particular treatment for which the bowl is utilized. Additionally, to avoid contamination of biological fluids, or exposure of persons involved in the processing operation to the fluids, the transfer operations are preferably carried out within a sealed flow system, possibly pressurized, preferably formed of flexible plastic or similar material which can be disposed of after each use.

Figure 2:
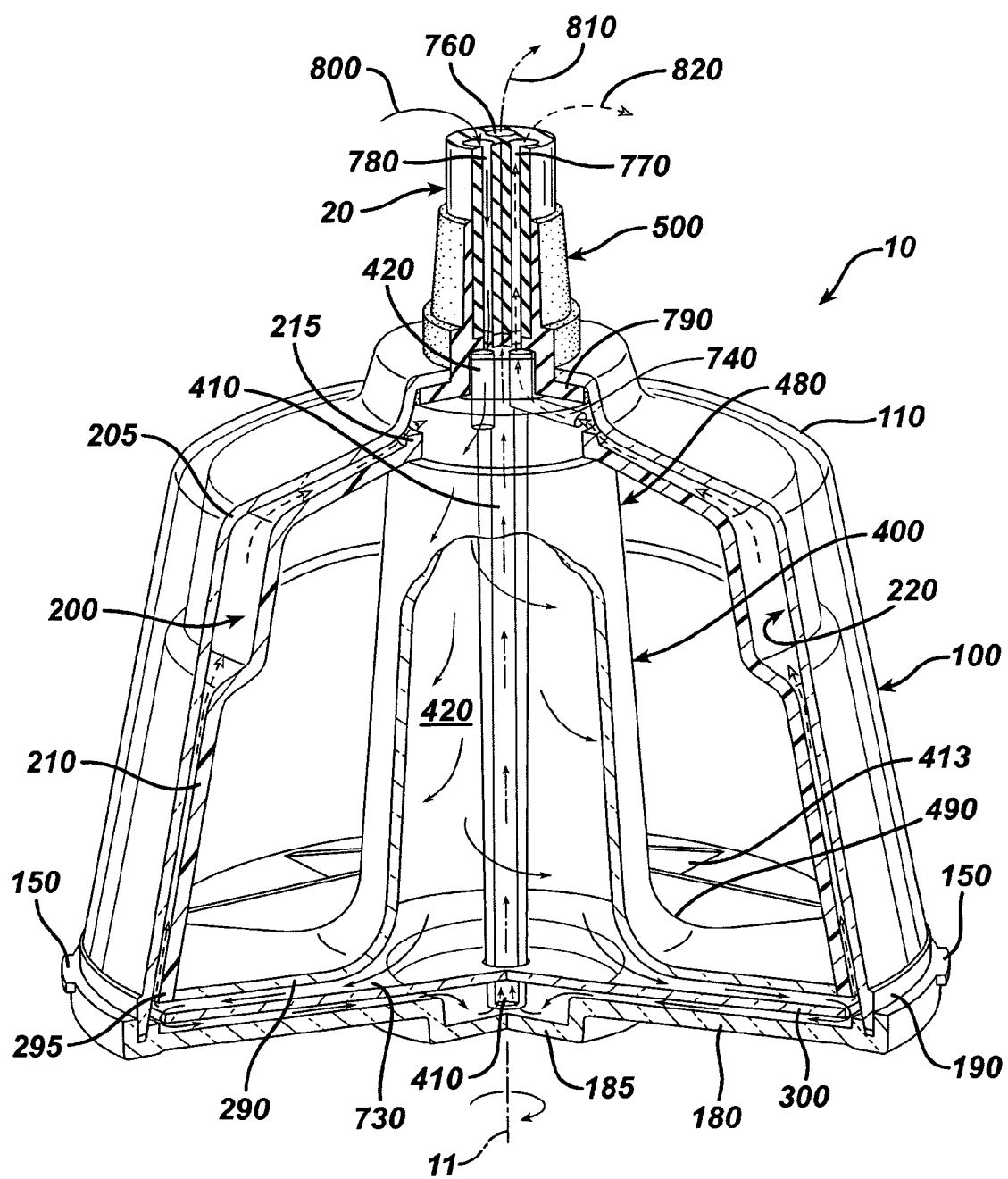
FIG. 2 is a front elevational view of the apparatus of FIG. 1 partially in section.

Referring to FIG. 2, outer housing 100 is substantially conical-shaped with an upper housing end 110 and a lower housing end 190. Outer housing 100 may be made of plastic (such as those plastics listed previously), or any other suitable material. Upper housing end 110 preferably has a neck 115. Neck 115 forms housing outlet 700 (FIG. 4) which is sized to secure and hold sleeve flange 790 of connection sleeve 500. However connection sleeve 500 can be secured to bowl 10 by any suitable means, including for example, a lip, groove, or tight fit and adhesive with a component of bowl 10. Lower housing end 190 has a housing floor 180 of greater diameter than upper end 110. Housing floor 180 may have an indentation 185 that is used to collect denser fluid 810. The diameter of outer housing 100 increases from upper housing end 110 to lower housing end 190.

Figure 18:
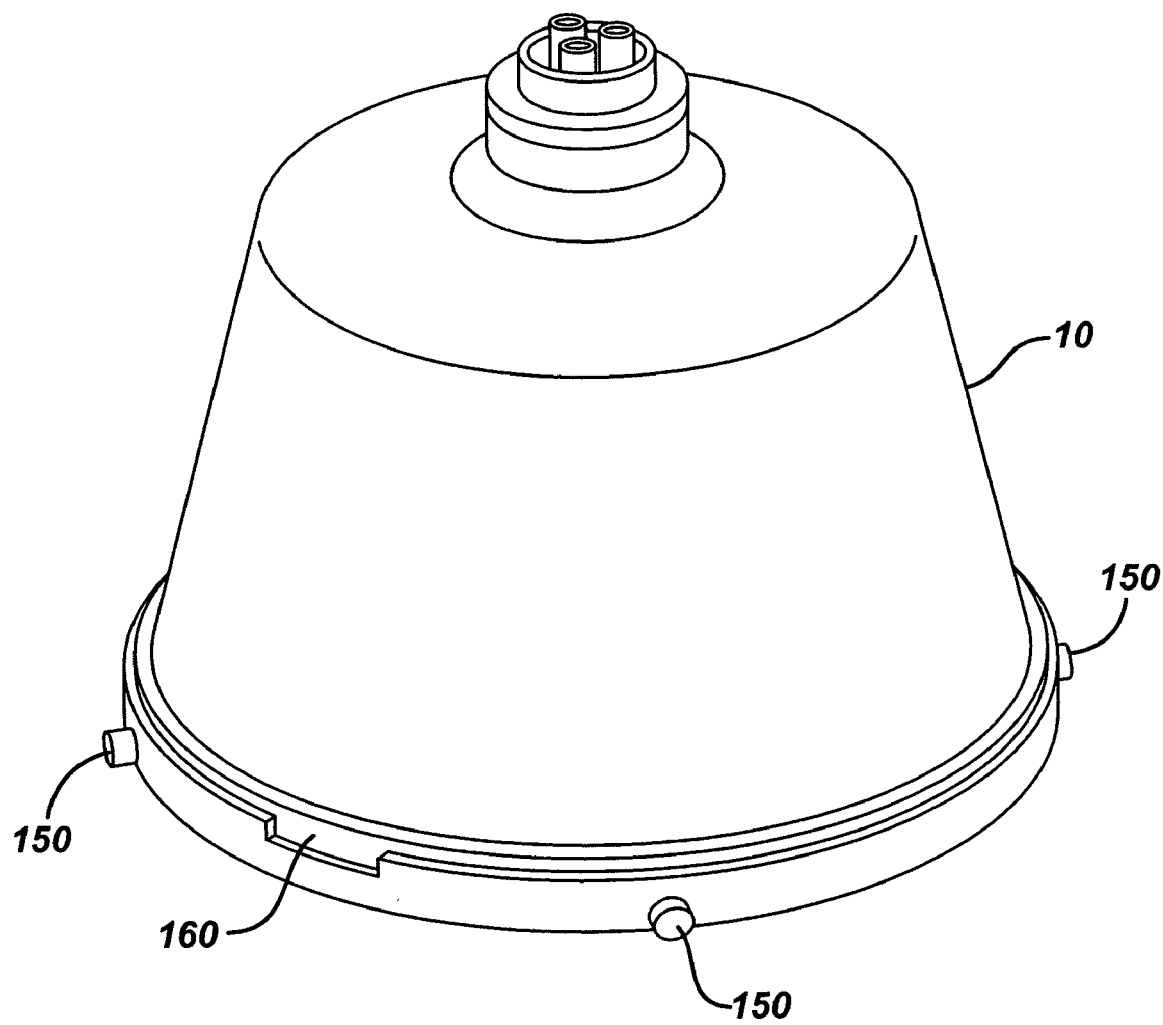
FIG. 18 is a perspective view of a second embodiment of a centrifuge bowl according to the present invention.

Outer housing 100 is adapted to rotatably connect to a rotational device 900 (FIG. 12), such as for example, a rotor drive system or a rotating bracket 910. The rotatable connection may, for example, be a bearing that allows free rotation of bowl 10. Outer housing 100 preferably has a locking mechanism. The locking mechanism may be one or more protrusions 150 designed to interact with corresponding indentations in a centrifuge container or any other suitable interconnect or locking mechanism or equivalent known in the art. The locking mechanism may also comprise a key slot 160 (FIG. 18).

Figure 4:
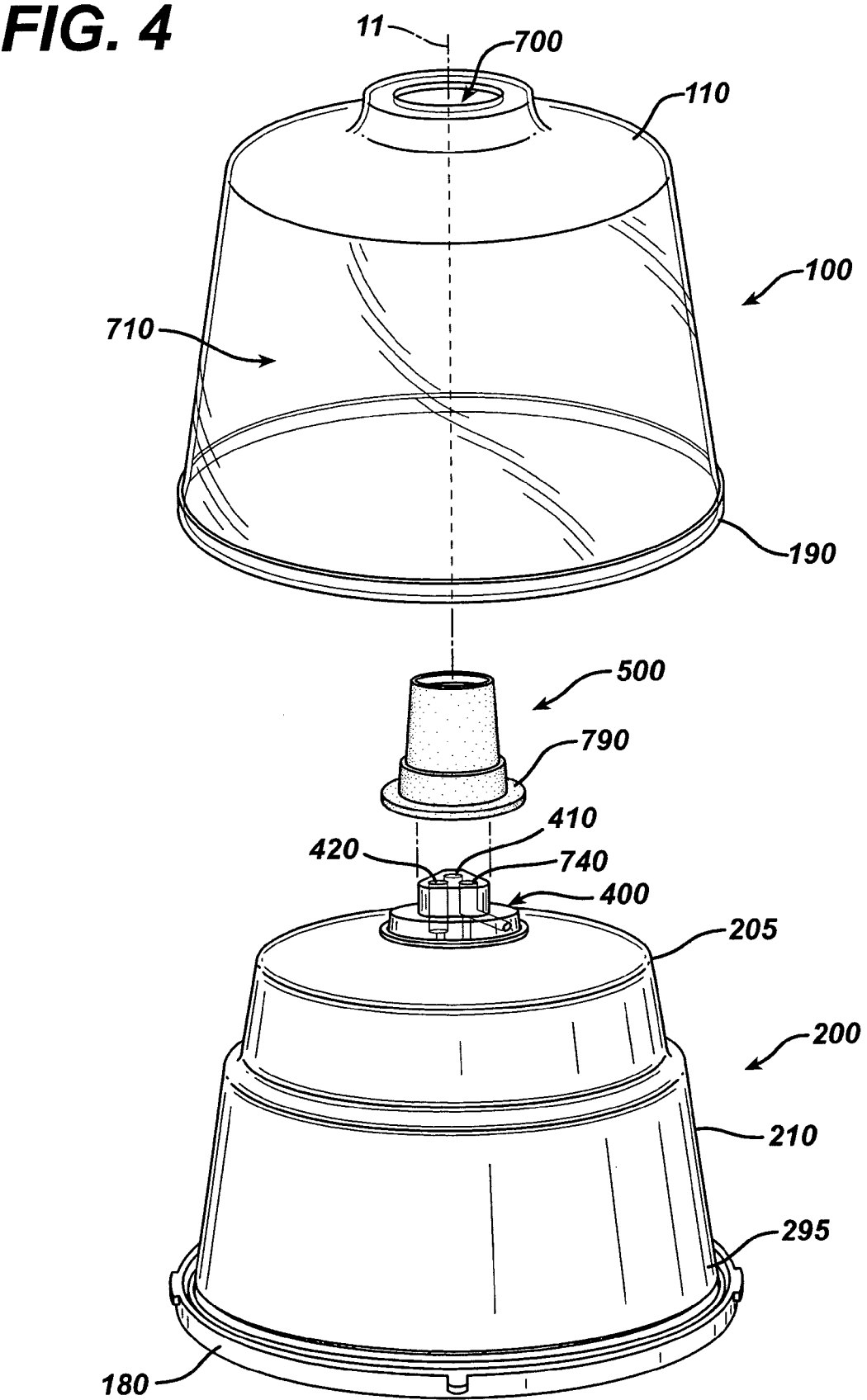
FIG. 4 is a front elevational view of the centrifuge bowl and connection sleeve of FIG. 1, wherein the connection sleeve and outer housing are exploded.

Referring to FIG. 4, outer housing 100 has an interior volume 710 in which core 200 will fit when bowl 10 is assembled. In assembling bowl 10, connection sleeve 500 is first mounted to lumen 400. Upon outer housing 100 being connected, connection sleeve 500 extends through housing outlet 700 until sleeve flange 790 engages outer housing 100 near upper housing end 110. When fully assembled, core 200 is fully within interior volume 710 of outer housing 100, occupying a coaxial volume of interior volume 710 about axis 11.

Referring back to FIG. 2, bowl 10 comprises core 200 positioned inside of outer housing 100 as described above. Core 200 has an outer wall 210 that is a stacked-conical shape that follows the general shape of outer housing 100. In an alternative embodiment, outer wall 210 may be a truncated cone-shape that is substantially smooth. The interior of core 200 is hollow, but may be solid if so desired. Interior wall 210 of core 200 provides a hollow cylindrical section for lumen 400 to pass through. Core 200 also comprises upper and lower core ends 205 and 295, respectively. Lower core end 295 has a core floor 290. The diameter of core 200 preferably increases from upper core end 205 to lower core end 295. Upper core end 205 of core 200 has a neck 215 fitted around the outside diameter of multi-axial lumen 400.

Figure 5:
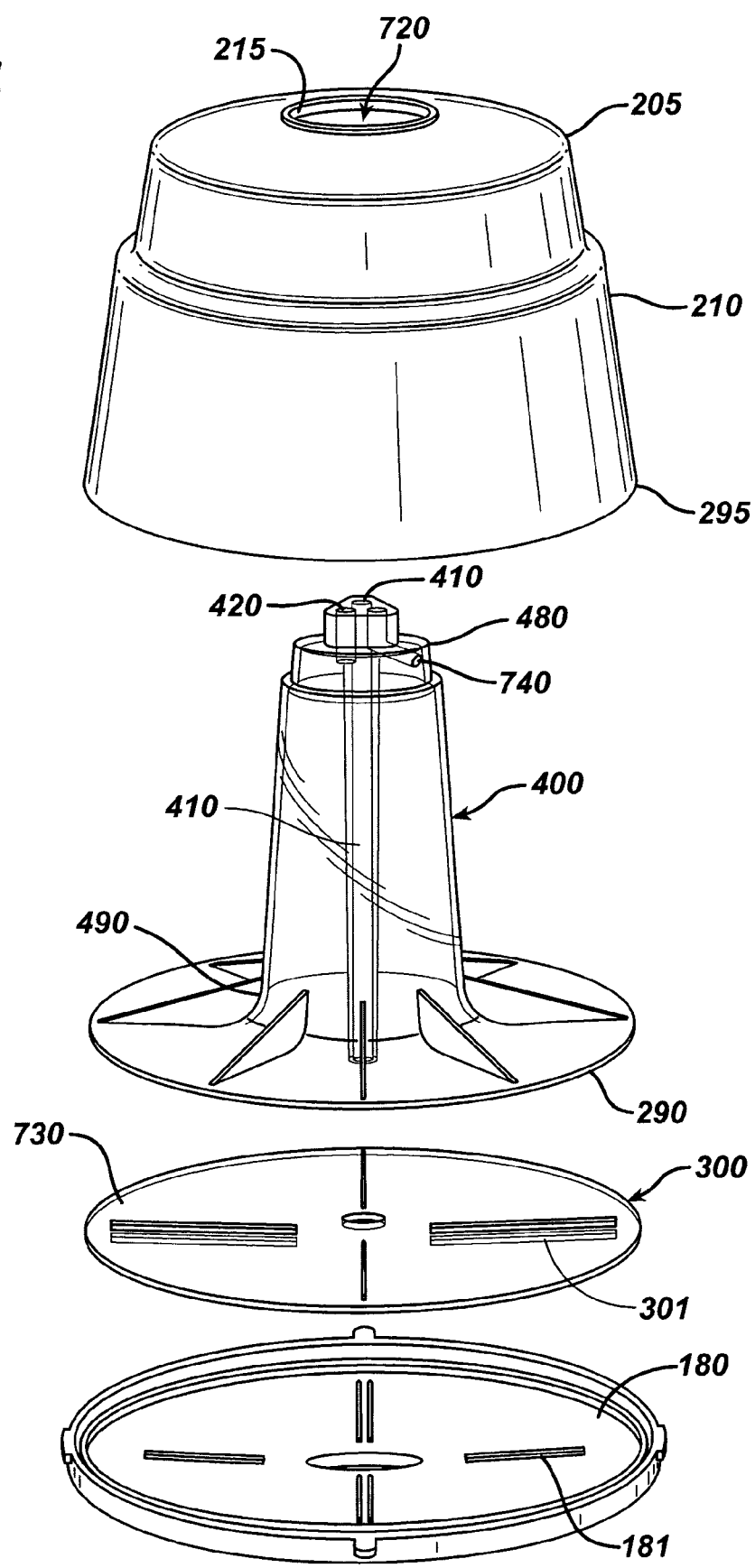
FIG. 5 is an exploded view of the centrifuge bowl of FIG. 1.

Referring to FIG. 5, neck 215 of core 200 forms core outlet 720 near upper core end 205. Core outlet 720 is sized so that lumen 400 can extend therethrough when assembled. In one embodiment of bowl 10, core floor 290 and lumen 400 are molded so as to be a single structure and having a plurality of fins 250 that provide support for lumen 400. Alternatively, bowl 10 can be constructed so that core floor 290 and lumen 400 are separate pieces. In such an embodiment, core floor 290 will have an opening through which lumen 400 will extend therethrough. This alternative embodiment makes it possible for bowl 10 to be adapted so that core 200, outer housing 100, and lower plate 300 can rotate about a stationary lumen 400.

Referring back to FIG. 2, core 200 is positioned inside outer housing 100, occupying a coaxial volume of interior volume 710 of bowl 10 and forming separation volume 220 between outer wall 210 of core 200 and outer housing 100. Separation volume 220 is that space of interior volume 710 that is between core 200 and outer housing 100.

Figure 3:
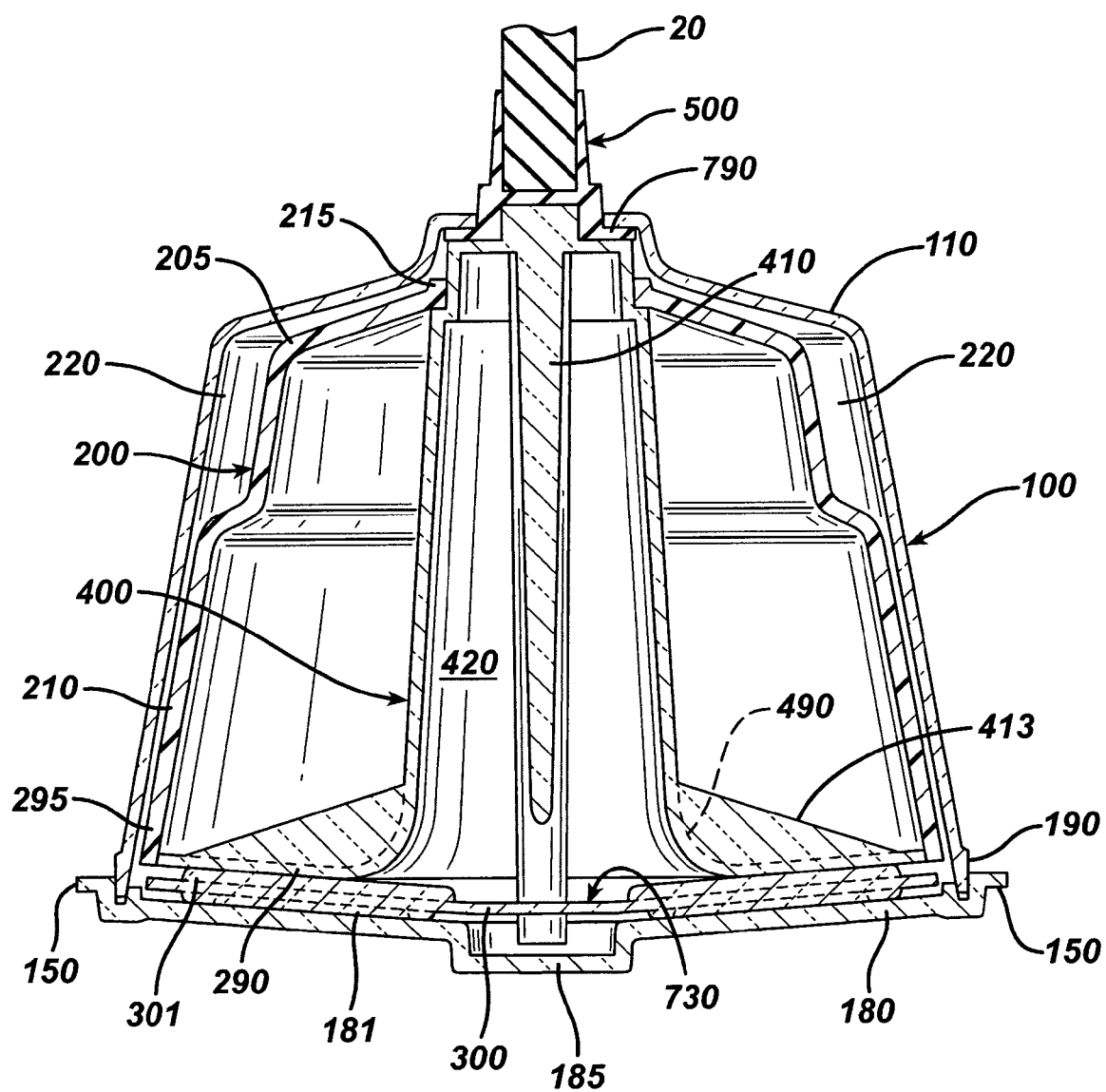
FIG. 3 is a cross-sectional view of the apparatus of FIG. 1 along line III-III.

Bowl 10 further comprises lower plate 300 having top surface 730. Lower plate 300 is positioned within separation volume 220 beneath core floor 290 and above housing floor 180. Lower plate 300 is circular and curves upward radially from its center (illustrated in FIG. 3). Alternatively, lower plate 300 can be flat. When positioned between core floor 290 and housing floor 180 as stated above, space still exists both between lower plate 300 and core floor 290 and between lower plate 300 and housing floor 180. These spaces allow fluid 800 to flow along top surface 730 of lower plate 300 and further allows a first separated fluid component 810 to flow under lower plate 300 atop housing floor 180. Top surface 730 of lower plate 300 may also have protrusions, indentations, or other guides that extend from the center of lower plate 300 radially outward to the edge of plate 300 to direct fluid 800 outward. Lower plate 300 may be made of plastic or any other suitable material. Lower plate 300 has opening 302 (FIG. 5) near its center through which that portion of lumen 400 that forms second bowl channel 410 extends. Opening 302 can be sized to form a tight fit with this portion of lumen 400 which will hold lower plate 300 suspended above housing floor 180.

Multi-axial lumen 400 is located inside core 200. Lumen 400 has an upper lumen end 480 and a lower lumen end 490 wherein the diameter of lumen 400 increases from upper lumen end 480 to lower lumen end 490. In the illustrated embodiment lumen 400 comprises first bowl channel 420, second bowl channel 410, and third bowl channel 740. First bowl channel 420 provides a passageway through lumen 400 to top surface 730 of lower plate 300 for the inflow of fluid 800. Second bowl channel 410 is located inside first bowl channel 420 and is completely enclosed therein. Second bowl channel 410 forms a passageway through lumen 400 from below lower plate 300 for the removal of a first separated fluid component 810 that gathers in indentation 185 of housing floor 180. Third bowl channel 740 forms a passage way through lumen 400 from separation volume 220 above lower plate 300 for the removal of second separated fluid component 820. Preferably, third bowl channel 740 forms a passageway from that portion of separation volume 220 that is at or near upper housing end 110. As illustrated, third bowl channel 740 is L-shaped. In alternative embodiments, first, second, and third bowl channels 820, 810, 740 can be placed at different positions on bowl 10. The bowl channels 820, 810, 740 may be arranged so as not to be all within lumen 400, so long as the necessary passageways are formed. For example, alternate configurations such as a single lumen partitioned into equal sections forming multiple lumens and/or fluid passageways will suffice. In another embodiment, there may be a non-coaxial bundle of lumens that are truncated in the appropriate sections of the centrifuge bowl. For example, the lumen carrying fluid 800 may be truncated below the bottom of the core 200 and above lower plate 300. Each bowl channel 820, 810, 740 may be made of any type of flexible or rigid tubing (such as medical tubing) or other such device providing a sealed passageway, possibly for pressurized or unpressurized fluid flow, and which preferably can be disposable and sterilizable, i.e., of simple and efficient manufacture.

Referring to FIG. 5, bowl 10 is adapted so that outer housing 100, core 200, lower plate 300, and lumen 400 are in connection and rotate together. Housing floor 180 of outer housing 100 (not illustrated in FIG. 5) comprises double ridges 181 on its top surface. Each double ridge 181 comprises two substantially parallel raised protrusions. Lower plate 300 has single ridges 301 on both its top surface 730 and bottom surface (not illustrated on bottom surface). Each single ridge 301 comprises a single raised linear protrusion. When assembled, each single ridge 301 on the bottom surface of lower plate 300 rests between and engages the two substantially parallel raised protrusions of a corresponding double ridge 181 on housing floor 180. Similarly, each single ridge 301 on top surface 730 of lower plate 300 will engage a corresponding double ridge 301 on the bottom surface of core floor 290 of core 200. Thus, when outer housing 100 is rotated, core 200, lower plate 300, and lumen 400 will rotate therewith.

Referring again to FIG. 2, connection sleeve 500 is secured to bowl 10 by means of sleeve flange 790. Connection sleeve 500 is also secured to external conduit 20 and is adapted to fluidly connect conduit channels 780, 760, 770 of external conduit 20 to bowl channels 420, 410, 740 of lumen 400 respectively. When assembled, connection sleeve 500 is mounted to lumen 400. Specifically, connection sleeve 500 is adapted to be mounted to lumen connector 481 (FIGS. 4 and 5).

Figure 7:
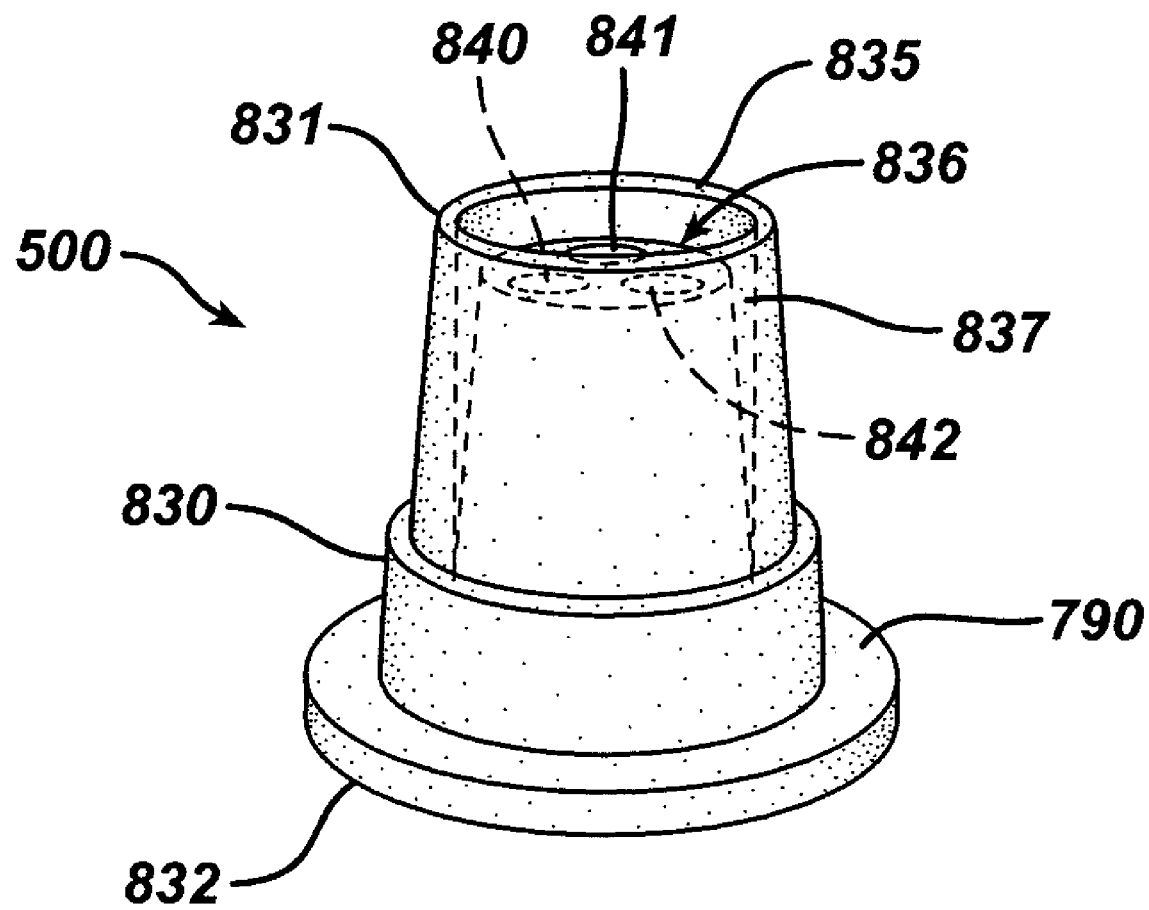
FIG. 7 is a front-elevational view of an embodiment of a connection sleeve according to the present invention.
Figure 10:
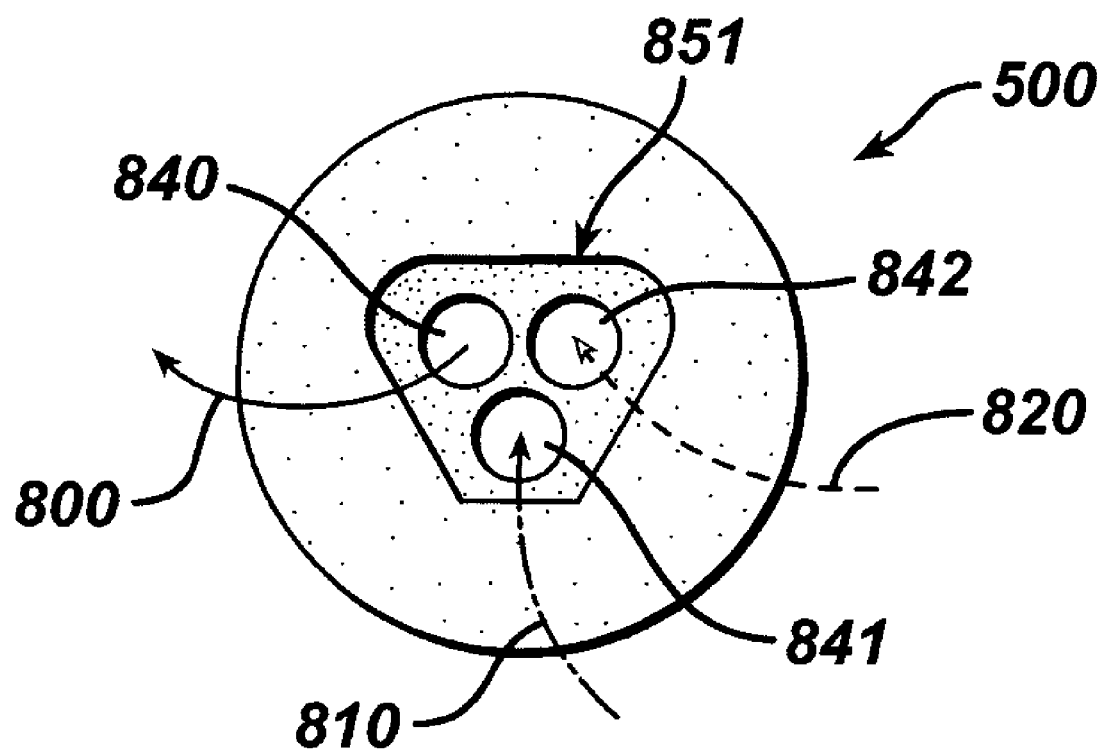
FIG. 10 is a bottom view of the connection sleeve of FIG. 7.

Referring now to FIGS. 7 and 10, connection sleeve 500 comprises body 830 having an upper sleeve end 831 and lower sleeve end 832. Lower sleeve end 832 has sleeve flange 790 which is sized to engage upper housing end 110 when body 830 of connection sleeve 500 is slidably inserted through housing outlet 700. Lower sleeve end 832 also comprises lumen mounting recess 851. Lumen mounting recess 851 is sized so that lumen connector 481 (FIG. 4) will fit tightly therein. Lumen mounting recess 851 is triangularly shaped but can take on any shape, so long as it corresponds in shape to that of lumen connector 481. However it is preferred that lumen mounting recess 851 not be circular. A circular shape would allow connection sleeve 500 to rotate about lumen 400, causing unwanted friction and possibly producing contaminants.

Figure 8:
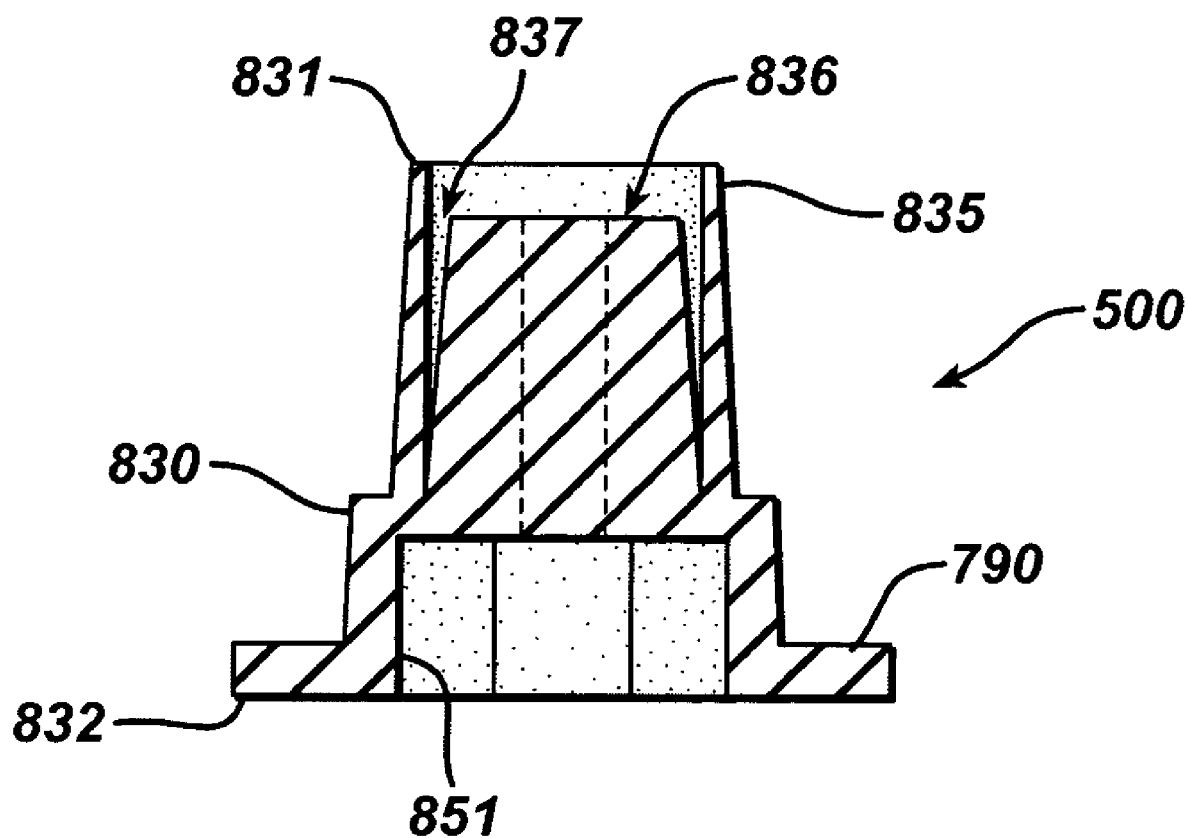
FIG. 8 is a cross-sectional view of the connection sleeve of FIG. 7 along line XIII—XIII.
Figure 9:
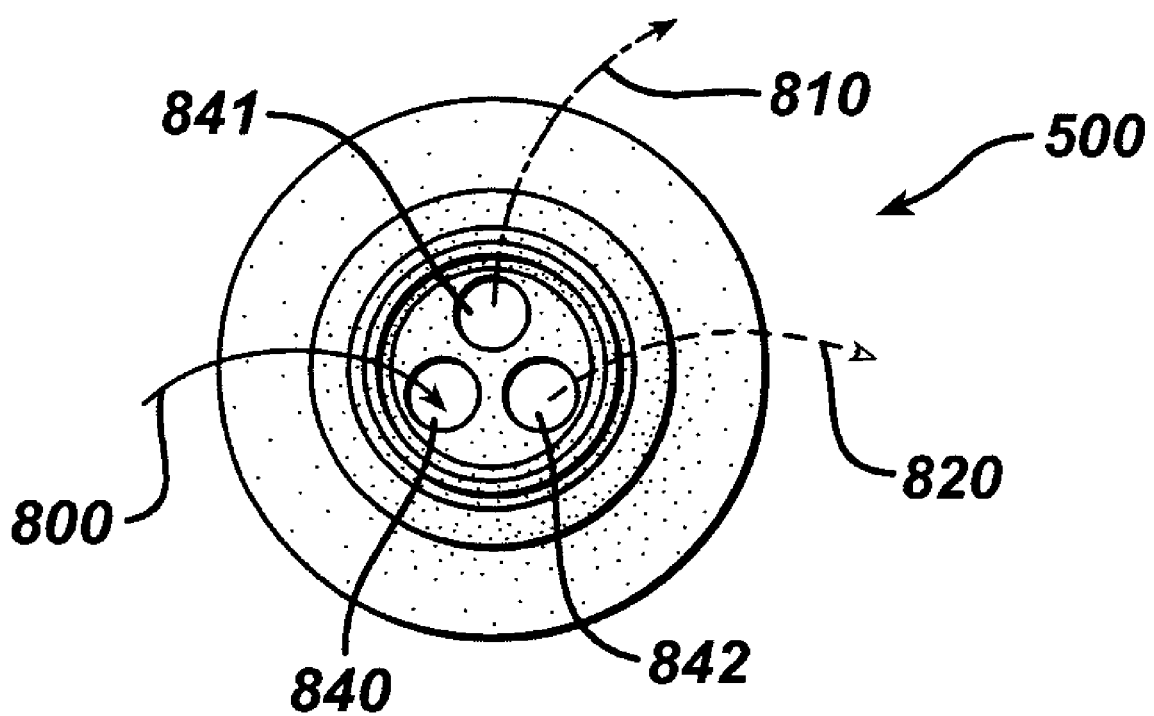
FIG. 9 is a top view of the connection sleeve of FIG. 7.
Figure 11:
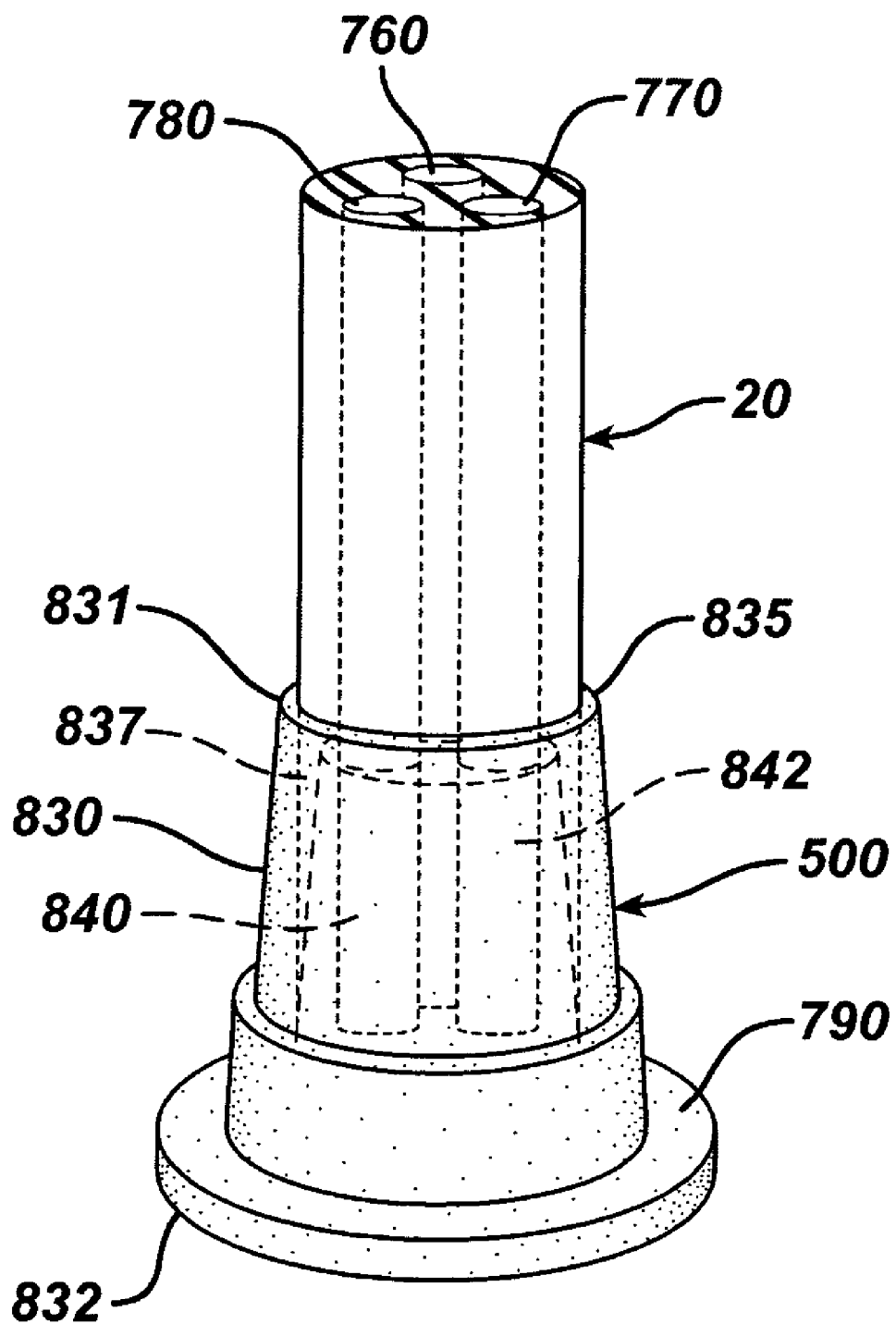
FIG. 11 is a top elevational view the connection sleeve of FIG. 7 having a portion of an external conduit fluidly secured to said connection sleeve.

Referring to FIGS. 7 and 8, upper sleeve end 831 is adapted to be secured to external conduit 20. Upper sleeve end 831 comprises wall 835 surrounding stub 836. Upper sleeve end 831 further comprises trench 837 positioned between wall 835 and stub 836. Trench 837 is preferably tapered. External conduit 20 is secured to connection sleeve 500 (as illustrated in FIG. 11) by sliding a raised outer wall portion of external conduit 20 into trench 837. Body 831 is sized and shaped so that when sleeve flange 790 engages outer housing 100, body 831 fits tight in housing outlet 700, protruding therefrom. This tight fit helps ensure that contagions do not enter bowl 10.

Referring to FIGS. 7 and 9–11, stub 836 comprises first stub channel 840, second stub channel 841, and third stub channel 842. First, second, and third stub channels 840, 841, 842 extend through stub 836, each forming a passageway through connection sleeve 500. When fluidly connect to external conduit 20 and bowl 10, first stub channel 840 fluidly connects first conduit channel 780 with first bowl channel 420 for inflowing fluid 800 from external conduit 20 into bowl 10 for separation. Similarly, second stub channel 841 fluidly connects second conduit channel 760 to second bowl channel 410 for removing first separated fluid component 810 from bowl 10 into external conduit 20. Finally, third stub channel 842 fluidly connects third conduit channel 770 to third bowl channel 740 for removing second separated fluid component 820 from bowl 10 into external conduit 20.

Connection sleeve 500 connects bowl 10 to external conduit 20 without use of a rotatable seal, which would otherwise normally be located between bowl 10 and connection sleeve 500. The seal-less connection between bowl 10 and connection sleeve 500 may occur as explained above or alternatively through use of, for example, an O-ring, a groove, or lip, grommet-type connection, welding, or a tight fit with or without adhesive in either bowl 10 or connection sleeve 500.

In order for bowl 10 to be used to separate fluid 800 into its higher and lower density components 810, 820 it is necessary that bowl 10 be rotated in a device capable of spinning bowl 10 at an adequate rotational velocity. However, this spinning must be achieved while still maintaining both the structural integrity of bowl 10 and all of the fluid connections between bowl 10, connection sleeve 500, and external conduit 20. For the present invention, rotation of bowl 10 without the use of a rotating seal is achieved through the use of 1-omeg 2-omega spin technology. The importance of 1-omega/2-omega spin technology is well known in the art, as seen for example, in U.S. Pat. No.

3,986,442, expressly incorporated by reference herein. Rotational devices utilizing 1-omega 2-omega spin technology allow bowl 10 and external conduit 20 to rotate without the use of a rotatable seal and eliminate any tangling of external conduit 20.

Figure 13:
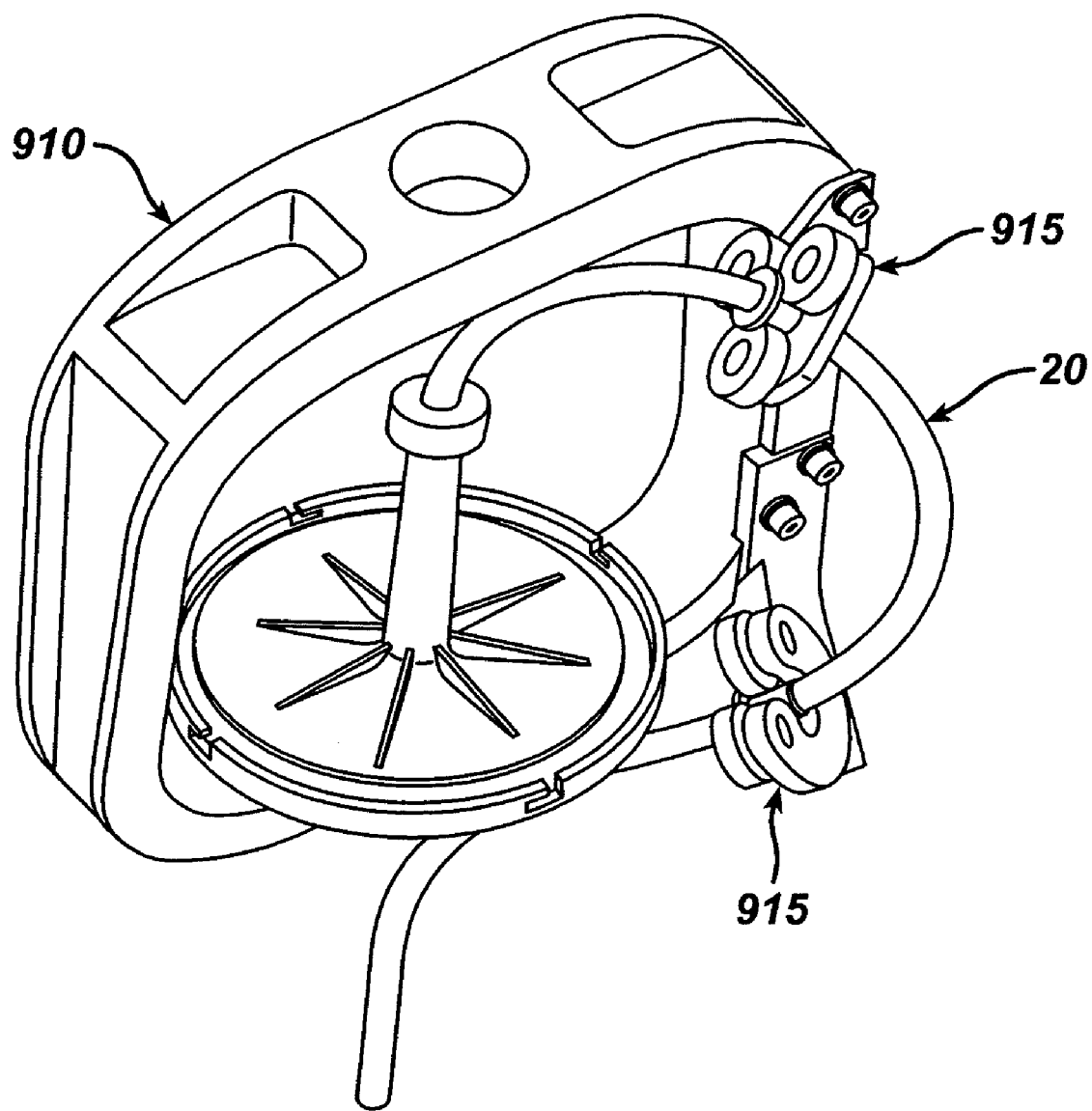
FIG. 13 is a perspective view of a bracket and rotational base of the rotational device of FIG. 12 with a portion of the centrifuge bowl of FIG. 1 positioned therein.

Referring to FIGS. 12 and 13, a rotational device 900 capable of utilizing 1-omega 2-omega spin technology is illustrated with bowl 10 positioned therein. Bowl 10 is rotatably connected to rotational device 900, which includes a rotating bracket 910 and an outer frame 914, both of which are, for example, made of aluminum or some other lightweight, sturdy metal. Rotating bracket 910 is rotatably connected to bowl 10 and has holders 915 (generically illustrated in FIG. 12) that restrain external conduit 20 in a specific configuration that resembles a "truncated reverse-S shape." Although external conduit 20 must maintain a particular configuration, it is still capable of loose rotation within holders 915. Thus, external conduit 20 is, for example, fed into holders 915. Holders 915 may have a wear plate designed to reduce friction and heat generated by friction between external conduit 20 and holder 915. Bracket 910 also has an opening through bottom ledge 916 that is designed to rotatably connect bowl 10 to bracket 910 to allow free rotation of bowl 10. This particular configuration allows external conduit 20 to act as a flexible shaft that transmits torque to bowl 10 and provides 2-omega spin. Rotating bracket 910 rotates while holding external conduit 20, providing 1-omega revolution, and is preferably driven by a motor 912 or some other energy source known in the art. Motor 912 has a drive shaft 913 that rotates. Drive shaft 913 is connected to and transmits torque to bracket shaft 911 through the use of a belt, chain, or other connection (not illustrated). Bracket shaft 911 in turn transmits rotational energy to bracket 910 and thus to bowl 10. External conduit 20 may be lightly restrained by restraint 918 located on outer frame 914.

Because the rotation and revolution of bracket 910 are in the same direction, this transposition of the bracket 910 results in summation of the rates of rotation and revolution. Consequently, the bracket rotates at half the speed of the bowl (1ω) around central axis 11, hence the term "1-omega." The bowl 10 rotates at twice the speed (2ω) of the bracket, hence the term "2-omega."

Alternatively, other rotational systems may be used such as that described in U.S. Pat. No. 3,986,442, which is expressly incorporated herein by reference in its entirety. This rotational system includes a drive system for the rotation of bowl 10. In this assembly, bowl 10 would be connected to a rotor assembly that is rotatably mounted on a rotor drive assembly that is rotatably mounted to a stationary base.

Figure 6:
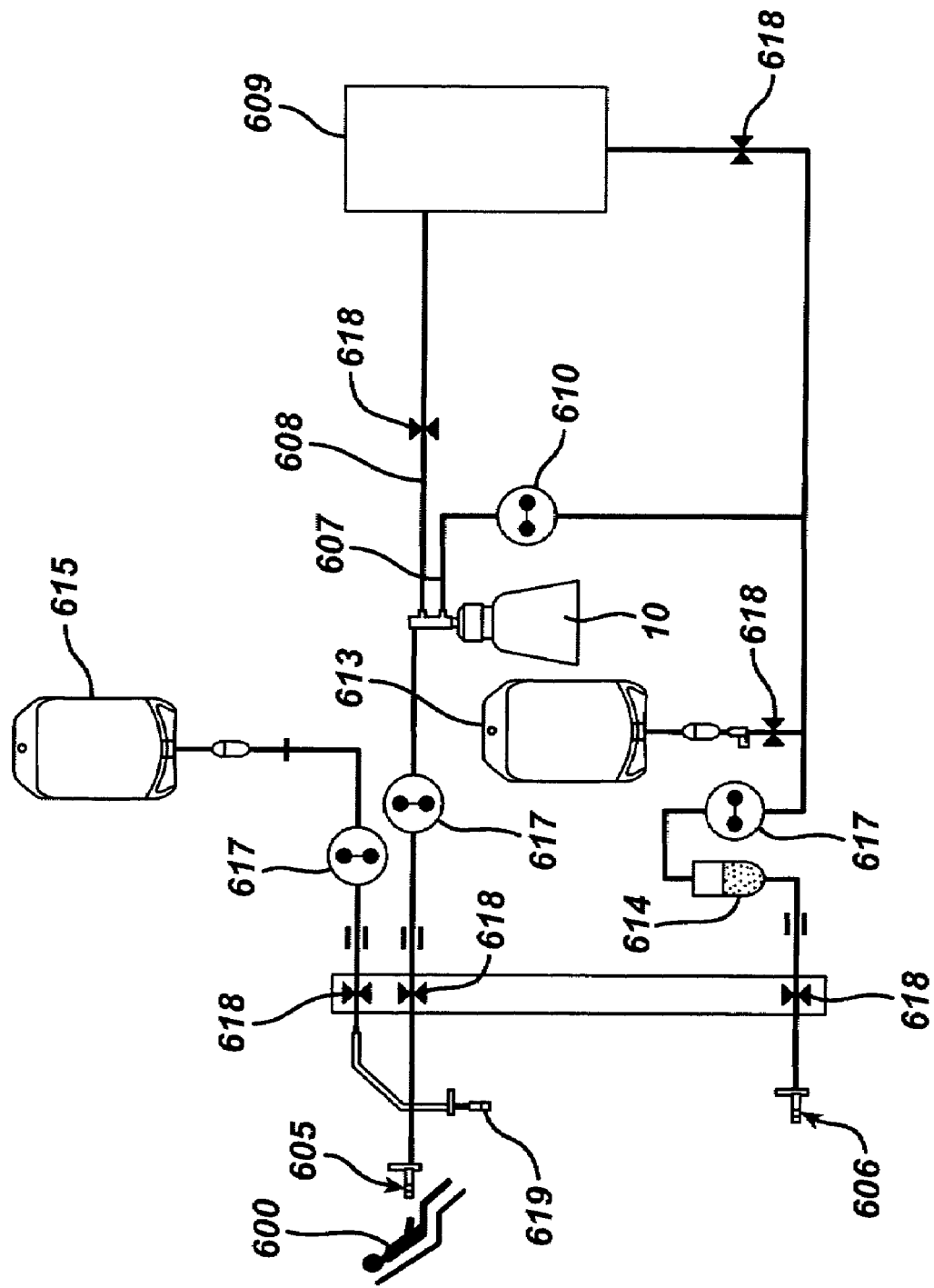
FIG. 6 is a schematic of one embodiment of the apparatus of the present invention, a closed-loop system for ameliorating, preventing, treating, or delaying the onset of diseases.

Bowl 10 and the rotational device 900 may be used in conjunction with a larger system, such as the closed-loop continuous flow system 630 depicted in FIG. 6. A source 600, such as a patient for example, is connected to system 630 by a needle or catheter 605. System 630 can be any suitable system that can be used to treat, ameliorate, prevent, or delay the onset of T-cell or white blood cell mediated diseases, such as a photopheresis-type unit. System 630 comprises anticoagulant source 615, centrifuge bowl 10 within rotational apparatus 900 (not illustrated), buffy coat treatment assembly 609, a plasma storage chamber (not illustrated), saline source 613, and drip chamber/filter 614. All of these elements are fluidly connected using sterile tubing so that a liquid, such as blood, can flow therethrough. System 630 can be adapted to be a closed-loop system by connecting return needle or catheter 606 to source 600 to reinfuse separated RBCs and treated buffy coat back into the source/patient 600.

System 630 has a plurality of pumps 617 strategically located to ensure proper pressures and continuous flow throughout system 630. In one embodiment of the present invention, an uninterrupted continuous flow pump is used, such as the pump described in U.S. patent application Ser. No. 09/389,463, herein incorporated by reference in its entirety. System 630 further comprises a plurality of flow regulation valves 618 located throughout system 630 to appropriately facilitate and control the flow of fluid through the fluid connections of system 630.

In utilizing system 630 to treat a patient for one of the aforementioned diseases or conditions, the treatment procedure begins when centrifuge bowl 10, possibly part of a disposable kit, is placed inside a photopheresis-type unit, or another suitable system, and is locked into rotational device 900 (FIG. 12) via protrusions 150 and/or key slots 160 by a twisting motion. Once bowl 10 is properly locked into place and fluidly connected to system 630, blood is drawn from patient 600 and into a sterile tubing set using needle 605. Anticoagulant is then added to the inflowing blood from anticoagulant source 615 in a proportion known in the art to prevent coagulation, such as, for example, disclosed in U.S. patent application Ser. No. 09/480,893, herein expressly incorporated by reference. The incoming whole blood, with a percentage of anticoagulant) then enters bowl 10.

Referring to FIG. 2, this incoming whole blood 800 enters rotating centrifuge bowl 10 by passing into first conduit channel 780 of external conduit 20, through first stub channel 840 (FIG. 9) of connection sleeve 500, and into first bowl channel 420 of bowl 10. Whole blood 800 flows downward through first bowl channel 420 until it reaches top surface 730 of lower plate 300 in separation volume 220. As bowl 10 is rotated about axis 11, centrifugal forces separate the whole blood 800 into a first separated fluid component 810 and second separated fluid component 820. Separated fluid components 810, 820 are separated into different fractions in accordance with the component densities. The higher density fluid component 810 comprises red blood cells ("RBCs") while the lower density component 820 comprises buffy coat (WBCs, platelets, and plasma). As bowl 10 continues to be rotated, the fluids/components flow outwardly along top surface 730 of lower plate 300 until reaching the edge of lower plate 300. At this point, the higher density component, which in the present embodiment is RBCs 810, falls to the bottom of bowl 10 and onto housing floor 180 of outer housing 100. As the RBCs 810 flow downward, due to their heavier weight, they flow in an opposite direction of the buffy coat 810, which may flow, for example, upwards. As RBCs 810 aggregate in the bottom of bowl 10, some RBCs 810 will eventually be pushed into and gather in indentation 185 in the center of housing floor 180 in that part of separation volume 220 below lower plate 300. Once gathered in indentation 185 below lower plate 300, the RBCs 810 are removed from bowl 10 by the RBCs 810 flowing upward through second bowl channel 410, through second stub channel 841 of connection sleeve 500, and into second conduit channel 760 of external conduit 760.

Meanwhile, the less dense blood component, buffy coat 820, begins to aggregate and rise through separation volume 220 because it is less dense. As more whole blood 800 enters bowl 10, the buffy coat 820 rises in bowl 10, forcing buffy coat 820 towards the top of separation volume 220. The buffy coat 820 enters third bowl channel 740, flowing upward out of bowl 10 via third bowl channel 740, through third stub channel 842 (FIG. 9) of connection sleeve 500, and into third conduit channel 770 of external conduit 20.

In an alternative embodiment, RBCs 810 may be removed from bowl 10 via a pumping means. In another alternative embodiment, buffy coat 820 may be prevented from exiting bowl 10 by any means known in the art, thus, for example, increasing the overall pressure in the bowl, forcing the RBCs 810 out of the bowl.

Bowl 10, via external conduit 20, may be continuously emptied of its contents (RBCs 810 and buffy coat 820) to prevent a pause in a treatment cycle, or a "batch-type" process. Because bowl 10 provides a more continuous separation system, the effective separation of the components should increase with respect to time. Again, the apparatus and methods of the present invention may also, for example, be used to remove platelets from blood in much the same way, with the exception that the platelets may be removed instead of buffy coat. In this particular alternative application, a surge-type technique may be used. In this technique, plasma may be flushed into the bowl to float platelets to the top of the separation volume for their removal. Additionally, the centrifuge apparatus and associated systems and methods may be automated by sensors, controllers, and other means of automation known in the art.

RBCs 810 and buffy coat 820 are preferably pumped or pushed out of bowl 10 and then continue to be used in a photopheresis treatment system, such as system 630.

Referring back to FIG. 6, external conduit 20 (not illustrated) is properly connected to system 630 so that the RBC's 810 flow into sterile tubing 607 and buffy coat 820 flows into sterile tubing 608 after leaving bowl 10. Once in tubing 608, buffy coat 820 flows into buffy coat treatment assembly 609 (generically illustrated) where it is properly processed for reinfusion back into source 600 for treatment or amelioration of the aforementioned conditions or diseases. Buffy coat treatment assembly 609 will comprise the equipment necessary to process the buffy coat 820 as necessary for proper patient treatment, such as a chamber for holding buffy coat 810 and a source of ultra-violet radiation adapted to expose the buffy coat 820 to UV radiation. The exact equipment and design of buffy coat treatment assembly 609 will depend on the exact treatment requirements of the patient as known to those skilled in the art. After being processed in treatment assembly 609, the buffy coat exits treatment assembly 609 for reinfusion into source/patient 600.

Upon leaving bowl 10, the RBCs 810 flow into tubing 607 to be directly reinfused into source/patient 600. Before reinfusing RBC's 810 and/or buffy coat 820 into patient 600 via needle or catheter 606, these fluids are flowed through drip chamber/filter 614. Saline can also be added to the fluids from saline source 613. When needle/catheter 606 is connected to patient 600, a closed-loop system is formed that can be used to continuously treat patient 600 without the need to batch-process blood 800. While needles/catheters 605 and 606 are illustrated as single lumen needles/catheters, it is possible to use a double lumen catheter in system 630 so that the same needle/catheter can be used to both remove and reinfuse fluids from the patient.

It has been discovered that increasing the time that buffy coat 810 is subjected to rotational motion in centrifuge bowl 10 yields a "cleaner cut" of buffy coat 820. A "cleaner cut" means that the hermatocrit count (HCT %) is decreased. HCT % is the amount of red blood cells present per volume of buffy coat. The amount of time that buffy coat 820 is subjected to rotational motion in centrifuge bowl 10 can be maximized in the following manner. First, whole blood 800 is fed into first bowl channel 420 as centrifuge bowl 10 is rotating. As discussed above, whole blood 800 is separated into buffy coat 820 and RBC's 810 as it moves outwardly atop lower plate 300. Second bowl channel 410 and third bowl channel 740 are closed at this time. The inflow of whole blood 800 is continued until the separation volume 220 is filled with a combination of buffy coat 820 near the top and RBC's 810 near the bottom of centrifuge bowl 10. By removing RBC's 810 from centrifuge bowl 10 via second bowl channel 410 only, additional volume is created for the inflow of whole blood 800 and the unremoved buffy coat 820 is subjected to rotational forces for an extended period of time. As centrifuge bowl 10 continues to rotate, some of the RBC's 810 that may be trapped in buffy coat 820 get pulled to the bottom of centrifuge bowl 10 and away from third bowl channel 740 and buffy coat 820. Thus, when third bowl channel 740 is opened, the buffy coat 820 that is removed has a lower HCT %. By controlling the inflow rate of whole blood 800 and the outflow rates of buffy coat 820 and RBC's 810, a steady state can be reached that yields a buffy coat 820 with an approximately constant HCT %.

The elimination of batch processing and the improved yields achieved by the current invention, have reduced the treatment time necessary to properly treat patients. For an average sized adult, 90–100 milliliters of buffy coat/white blood cells must be captured in order to conduct a full photophoresis treatment. In order to collect this amount of buffy coat/white blood cells, the present invention needs to process around 1.5 liters of whole blood. The required amount of buffy coat/white blood cells can be removed from the 1.5 liters of whole blood in about 30–45 minutes using the present invention, collecting around 60% or more of the total amount of the buffy coat/white blood cells that are subjected to the separation process. The captured buffy coat/white blood cells have an HCT of 2% or less. In comparison, one existing apparatus, the UVAR XTS, takes around 90 minutes to process 1.5 liters of whole blood to obtain the sufficient amount of buffy coat/white blood cells. The UVAR XTS only collects around 50% of the total amount of the buffy coat/white blood cells that are subjected to the separation process. The HCT of the buffy coat/white blood cells collected by the UVAR XTS is around, but not substantially below, 2%. Another existing apparatus, the Cobe Spectra™ by Gambro, must process 10 liters of whole blood in order to collect the sufficient amount of buffy coat/white blood cells. This typically takes around 150 minutes, collecting only 10–15% of the total amount of the buffy coat/white blood cells that are subjected to the separation process, and having an HCT of about 2%. Thus, it has been discovered that while existing apparatus and systems require anywhere from 152 to 225 minutes to separate, process, treat, and reinfuse the requisite amount of white blood cells or buffy coat, the present invention can perform the same functions in less than 70 minutes. These times do not include the patient preparation or prime time. The times indicate only the total time that the patient is connected to the system 630.

Referring back to FIG. 12, bowl 10 must be secured within rotational device 900 and allowed to rotate therein while remaining fluidly connected to system 630 (FIG. 6). As mentioned earlier, the use of a rotatable seal is undesirable. However, the cyclical rotation of bowl 10 and external conduit 20 can cause the fluid connection to fail in a variety of ways, including structural failure. In order to more effectively and efficiently fluidly connect bowl 10 to system 630, conduit assembly 860 (FIG. 14) is utilized.

Figure 14:
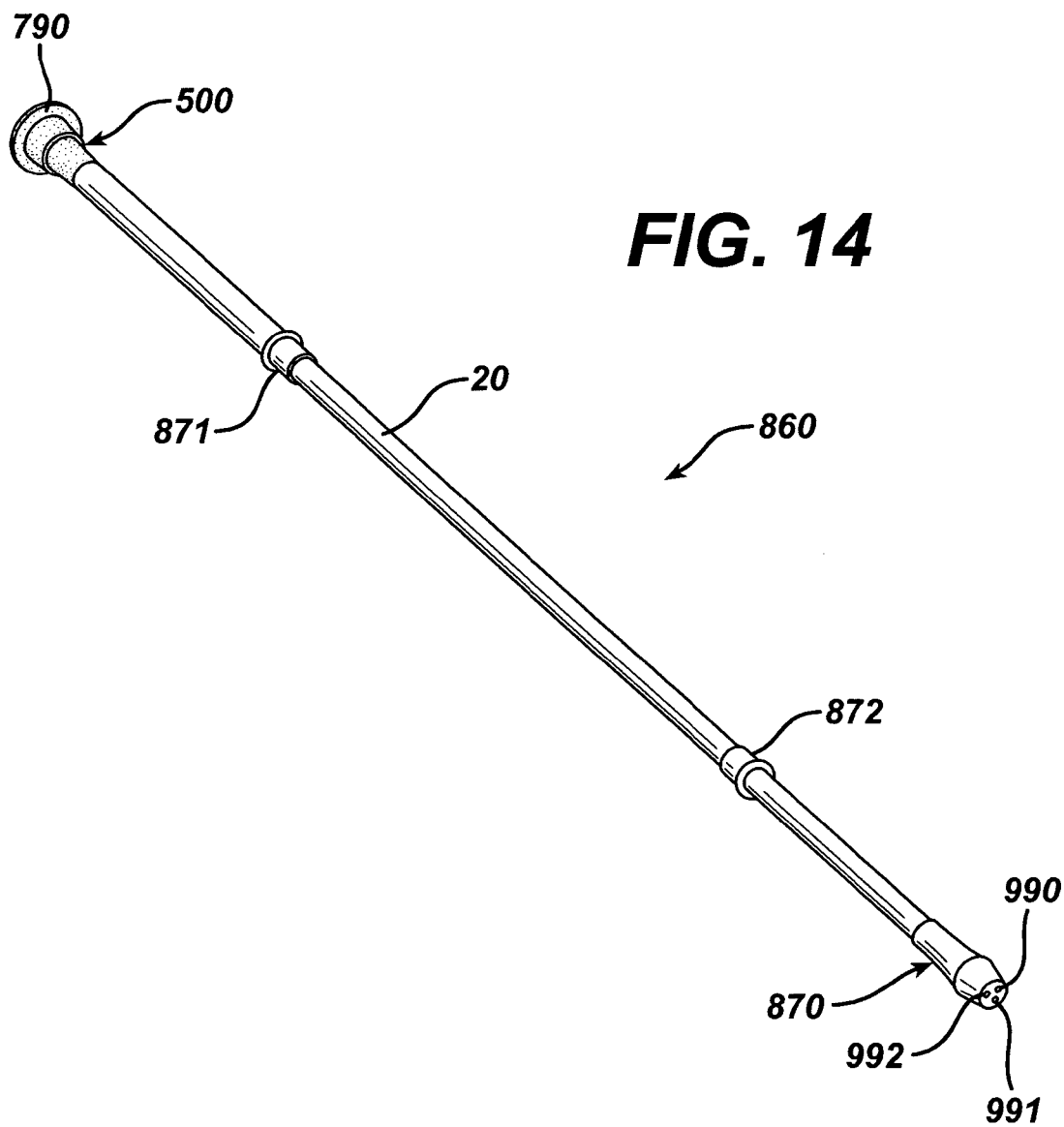
FIG. 14 is a perspective view an embodiment of a conduit assembly according to the present invention.

Referring to FIG. 14, conduit assembly 860 is illustrated. Conduit assembly 860 comprises external conduit 20, connection sleeve 500, anchor sleeve 870, and first and second bearing rings 871, 872. Connection sleeve 100 is adapted to be secured to bowl 10 when bowl 10 is in rotational device 900. Anchor sleeve 870 is connected in a stationary position to restraint 918 of rotational device 900 (FIG. 12) and fluidly connects external conduit 20 to the rest of system 630. Conduit assembly 860 further comprises first, second, and third assembly channels 990, 991, and 992 that extend through conduit assembly 860 and through which fluids can flow.

External conduit 20 has an approximately constant diameter. Constructing external conduit 20 to have a constant diameter helps reduce the problem of the external conduit being too rigid. An excessively rigid external conduit will heat up and fail more quickly. Additionally, a constant diameter conduit is cheap/easy to manufacture, allows easy experimentation with connection sleeve 500 and anchor sleeve 870 sizes, and allows bearing rings 871, 872 to be easily slid thereon. External conduit 20 may be made of any type of flexible tubing (such as medical tubing) or other such device providing a sealed passageway for the flow of fluids, which may be pressurized, into or out of a reservoir of any sort, and which preferably can be disposable and sterilizable.

Figure 16:
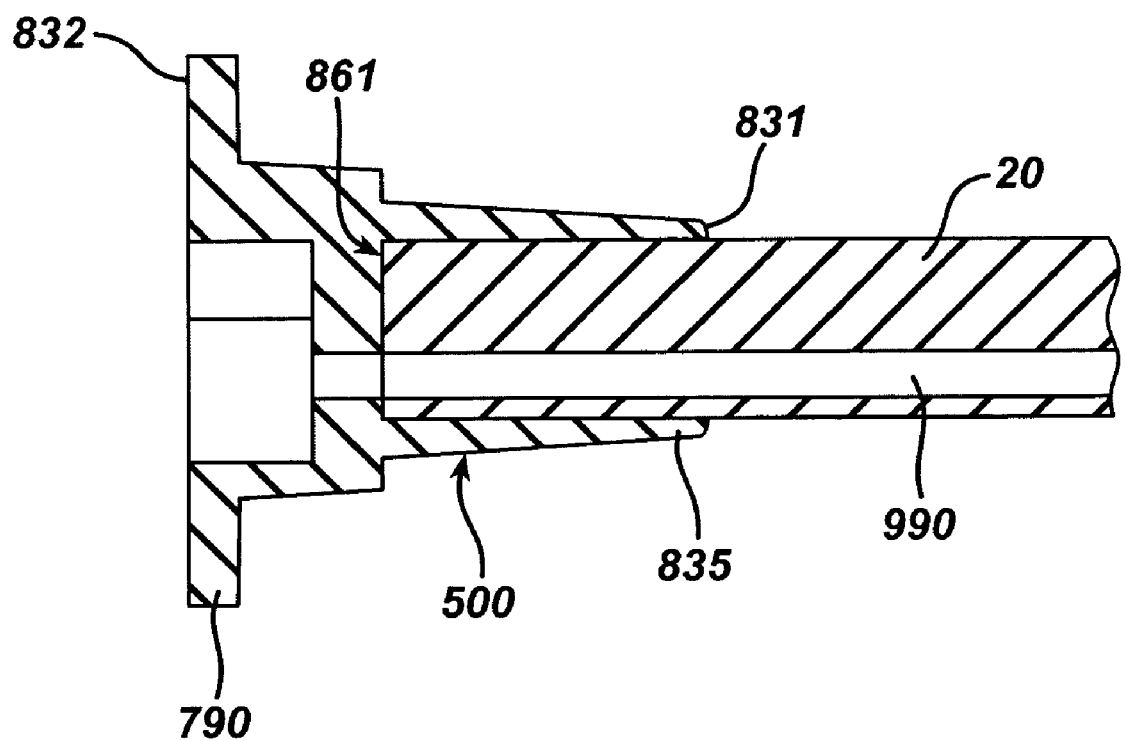
FIG. 16 is a cross sectional view of the connection sleeve of the conduit assembly of FIG. 15 along line XVII—XVII.

First and second bearing rings 871, 872 surround external conduit 20 and allow free rotation of external conduit 20 therein. When conduit assembly 860 is connected to bowl 10 and positioned in rotational device 900, external conduit 20 is supported by bracket 910 through the use of holders 915 which are generically illustrated in FIG. 12. Referring to FIG. 13, holders 15 can be roller assemblies adapted to engage ring bearings 871 and 872 so as to allow rotation of external conduit 20 therein. The positioning of ring bearings 871 and 872 on external conduit 20 is critical to the cyclical duration of the external conduit 20. For a centrifuge bowl having a height of 5 inches and a width of 5 inches, an external conduit having a length of approximately 21 inches is used. For this embodiment, it has been found that having first bearing ring 871 and second bearing 872 between 7.5 to 9.5 inches apart will increase the survival time of external conduit 20. Preferably first bearing ring 871 and second bearing 872 will be approximately 8.5 inches apart. It is also preferable that first bearing ring 871 be between 5.0 to 5.5 inches away from first end 832 of connection sleeve 500 (FIG. 16). These distances are exemplary only. Optimal distance/spacing measurements are dependent on the length of the external conduit, the size of the centrifuge bowl, and the spacing between and number of holder 15 used.

Figure 15:
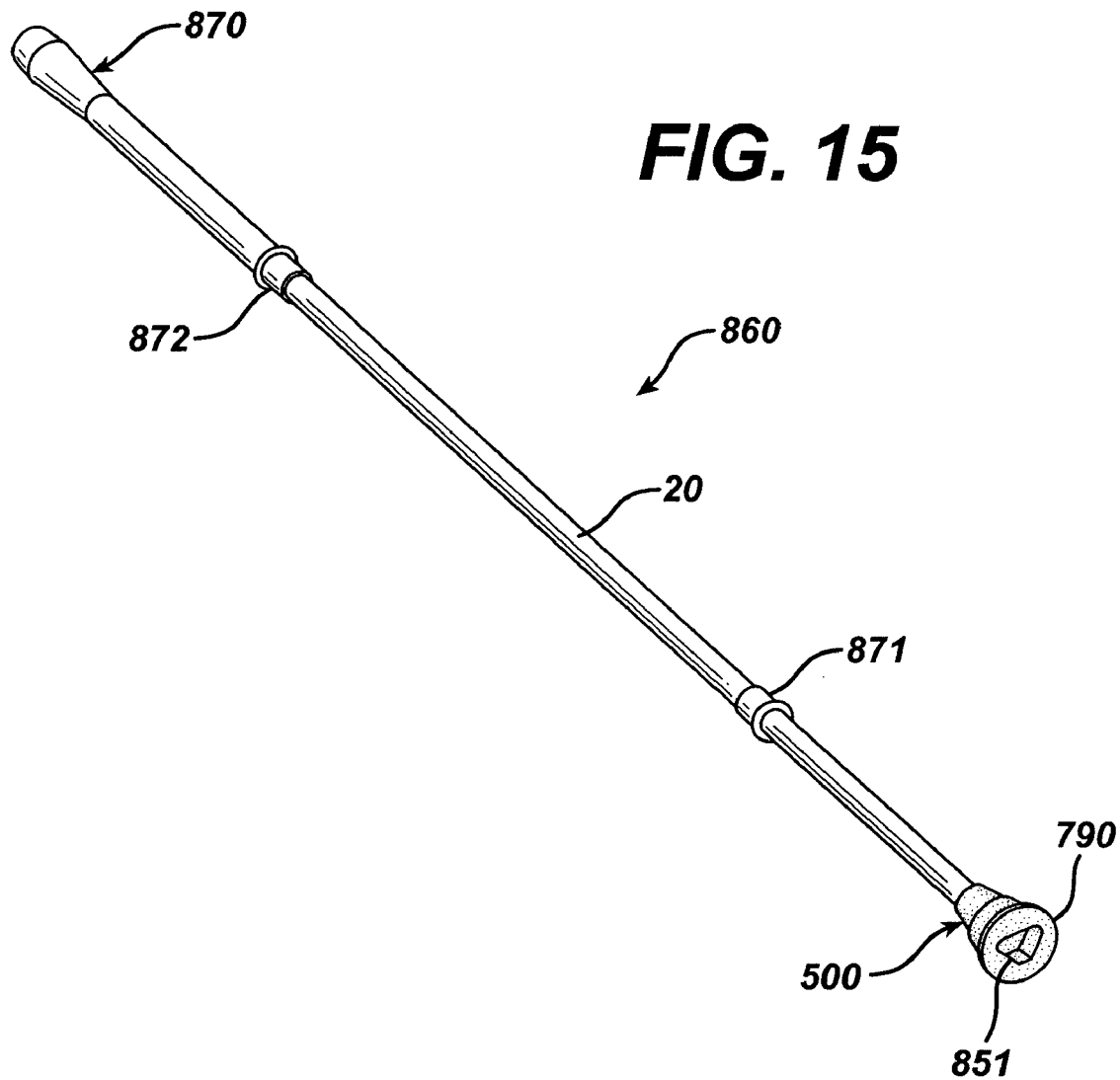
FIG. 15 is an elevated view of the conduit assembly of FIG. 14 from a different perspective.

Referring to FIG. 16, connection sleeve 500 has upper sleeve end 831 and lower sleeve end 832. Lower sleeve end 832 comprises sleeve flange 790 which can be used to secure connection sleeve 500 to centrifuge bowl 10, as described above. Lower sleeve end 832 also comprises lumen mounting recess 851 (FIG. 15). Lumen mounting recess 851 is adapted and sized to mount to a lumen 400 of a centrifuge bowl 10 as described above. Connection sleeve 500 preferably increases in diameter from upper sleeve end 831 to lower sleeve end 832 and is overmolded to first conduit end 861 of external conduit 20. The remaining characteristics of connection sleeve 500 of conduit assembly 860 are described above.

Figure 17:
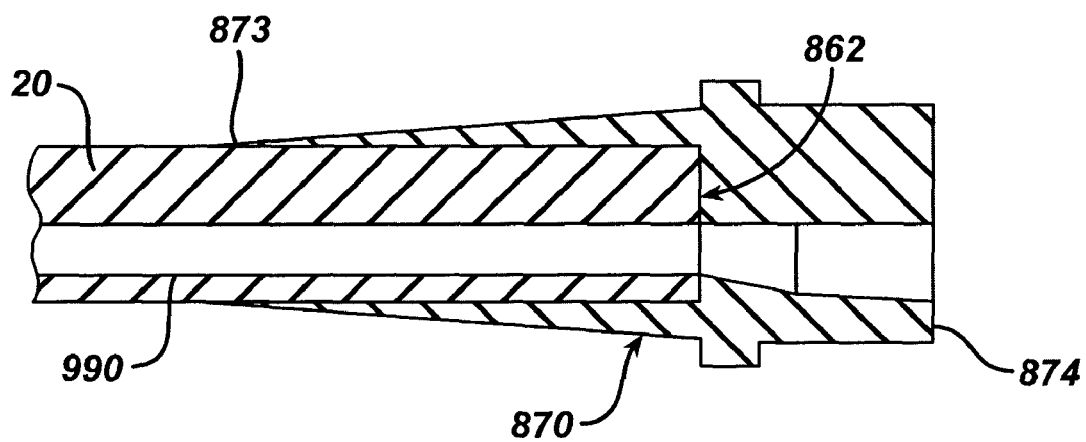
FIG. 17 is a cross sectional view of the anchor sleeve of the conduit assembly of FIG. 14 along line XVIII—XVIII.

Referring to FIG. 17, anchor sleeve 870 has first anchor end 873 and second anchor end 874. Anchor sleeve 870 is overmolded to second conduit end 862 of external conduit 20 and increases in diameter from first anchor end 873 to second anchor end 874.

Figure 19:
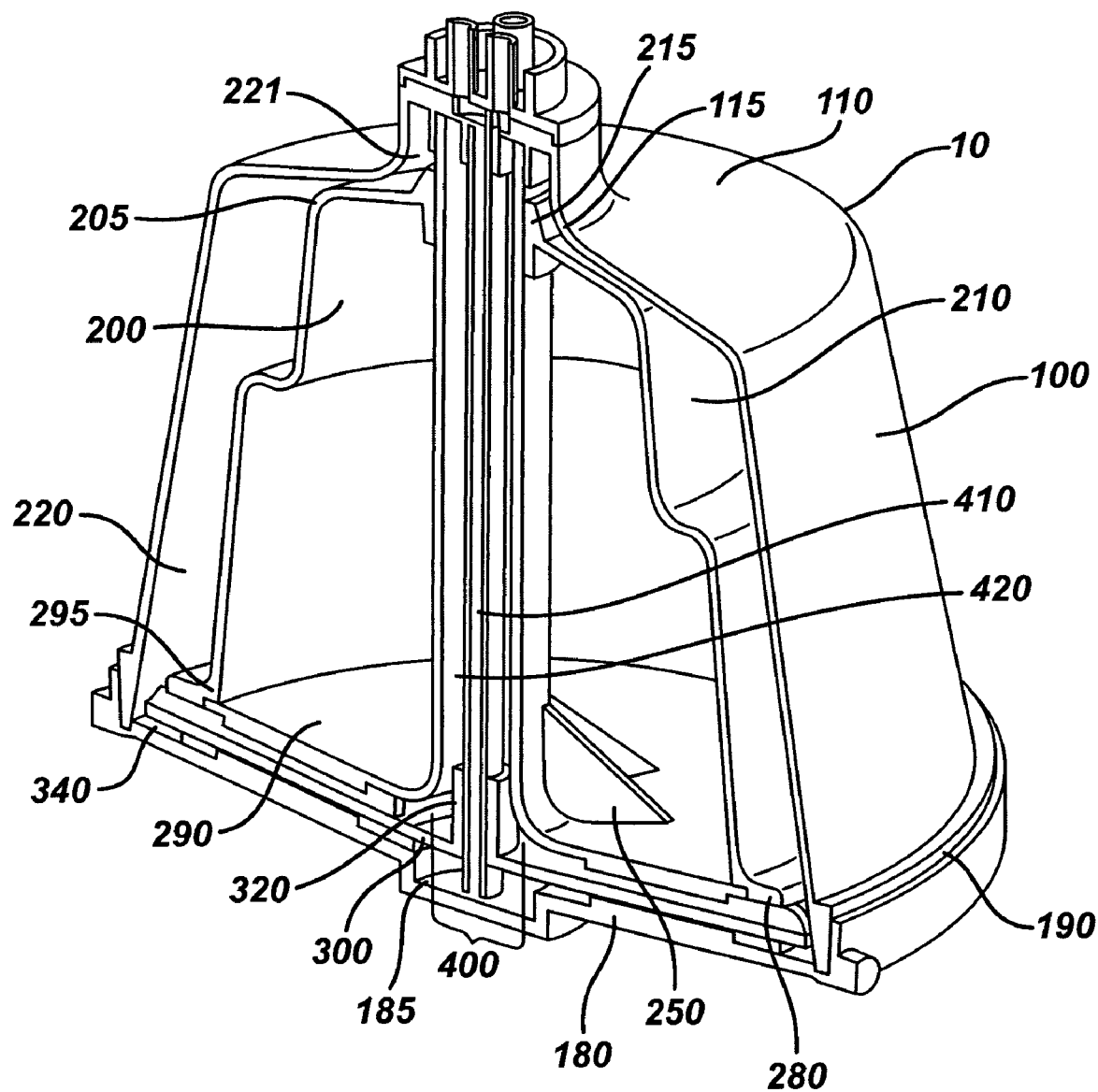
FIG. 19 is a perspective view of the apparatus of the centrifuge bowl of FIG. 18 partially in section.

FIGS. 18 and 19 illustrate a second embodiment of bowl 10. In order to avoid redundancy, only those important aspects of the second embodiment that differ from the first embodiment will be discussed. Referring to FIG. 18, the locking mechanism for securing the second embodiment of bowl 10 to rotational device 900 comprises both protrusions 150 and key slots 160.

Referring now to FIG. 19, core floor 290 of core 200 extends past outer wall 210 into separation volume 220 and provides, for example, a curved floor flange 280. When using this second embodiment to separate blood into its components, the curve of floor flange 280 may helps to move the buffy coat upward, possibly acting as a barrier to the buffy coat, thereby preventing the buffy coat from being dragged by the RBCs.

Additionally, lower plate 300 may comprise hollow cylinder 320. In another embodiment, hollow cylinder 320 may be more than one cylinder stacked on top of each other having various diameters and heights. Hollow cylinder 320 has an outer diameter substantially less than lower plate 300 and is adapted to surround lumen 400 by tight fit and holds lower plate 300 suspended above housing floor 180. Second channel 410 extends from housing floor 180 of outer housing 100 through hollow cylinder 320 to connection sleeve 500. Hollow cylinder 320 provides a tight fit around inner lumen 410, providing support for lumen 400 at its lower end.

Other embodiments of the invention will be apparent to those skilled in the art from consideration of the specification and the practice of the invention disclosed herein. It is intended that the specification and examples be considered as exemplary only, with a true scope and spirit of the invention being indicated by the following claims. It will further be apparent to those skilled in the art that this apparatus need not be limited to just the separation of whole blood. Other fluids requiring particle separation may also be treated by the methods, systems, and apparatus described herein. It will also be evident that the upward orientation of certain apparatus components could be altered to permit orientation of lumens and the connection sleeve in a downward direction.

What is claimed is:

1. An apparatus for separating components of a fluid (800) comprising:
    an outer housing (100) with an upper housing end (110) and a lower housing end (190), wherein said outer housing (100) increases in diameter from said upper housing end (110) to said lower housing end (190), said lower housing end (190) having a housing floor (180) and said housing upper end (110) having a housing outlet (700), said outer housing (100) having an interior volume (710) and adapted for rotation about a center axis (11);
    a core (200) connected with said outer housing (100) for rotation therewith; having an outer wall (210) having an upper core end (205) and a lower core end (295), said lower core end (295) having a core floor (290) and said upper core end (205) having a core outlet (720); occupying a coaxial volume of said interior volume (710) of said outer housing (100), and providing a separation volume (220) between said core (200) and said outer housing (100);
    a lower plate (300) having a top surface (730), said lower plate (300) positioned within said separation volume (220), beneath said core floor (290) and above said housing floor (180);
    a lumen (400) positioned inside said core (200), said lumen (400) extending axially through said core (200);

a first bowl channel (420) within said lumen (400) to said top surface (730) of said lower plate (300) for inflowing said fluid (800);

a second bowl channel (410) from within said separation volume (220) beneath said lower plate (300) for removing a first separated fluid component (810), and a third bowl channel (740) from said separation volume (220) above said lower plate (300) for removing a second separated fluid component (820)

wherein the housing, core, and plate rotate when said apparatus is rotated, said outer housing (100) comprises a locking mechanism adapted to secure said outer housing (100) to a rotational device, and wherein said locking mechanism comprises protrusions (150).

2. The apparatus of claim 1 wherein said locking mechanism comprises a key slot (160).

3. The apparatus of claim 1 wherein said apparatus (10) is adapted for use without a rotatable seal.

4. An apparatus for separating components of a fluid (800) comprising:

an outer housing (100) with an upper housing end (110) and a lower housing end (190), wherein said outer housing (100) increases in diameter from said upper housing end (110) to said lower housing end (190), said lower housing end (190) having a housing floor (180) and said housing upper end (110) having a housing outlet (700), said outer housing (100) having an interior volume (710) and adapted for rotation about a center axis (11);

a core (200) connected with said outer housing (100) for rotation therewith; having an outer wall (210) having an upper core end (205) and a lower core end (295), said lower core end (295) having a core floor (290) and said upper core end (205) having a core outlet (720); occupying a coaxial volume of said interior volume (710) of said outer housing (100), and providing a separation volume (220) between said core (200) and said outer housing (100);

a lower plate (300) having a top surface (730), said lower plate (300) positioned within said separation volume (220), beneath said core floor (290) and above said housing floor (180);

a lumen (400) positioned inside said core (200), said lumen (400) extending axially through said core (200);

a first bowl channel (420) within said lumen (400) to said top surface (730) of said lower plate (300) for inflowing said fluid (800);

a second bowl channel (410) from within said separation volume (220) beneath said lower plate (300) for removing a first separated fluid component (810), and a third bowl channel (740) from said separation volume (220) above said lower plate (300) for removing a second separated fluid component (820) wherein the housing, core, and plate rotate when said apparatus is rotated, and further comprising a rotational device that comprises a bracket (910).

5. The apparatus of claim 4 wherein said bracket (910) is adapted to engage and rotate an external conduit (20) that is fluidly connected to said first bowl channel (420), said second bowl channel (410), and said third bowl channel (740).

6. The apparatus of claim 5 wherein said rotational device is adapted to rotate said outer housing (100) and said external conduit (20) using 1-omega/2-omega spin technology.

* * * * *